(12) United States Patent
Haydar

(10) Patent No.: US 6,747,039 B2
(45) Date of Patent: Jun. 8, 2004

(54) AZA-BENZOTHIOPYRANOINDAZOLES WITH ANTITUMOR ACTIVITY

(75) Inventor: Simon N. Haydar, Niskayuna, NY (US)

(73) Assignee: Albany Molecular Research, Inc., Albany, NY (US)

(*) Notice: Subject to any disclaimer, the term of this patent is extended or adjusted under 35 U.S.C. 154(b) by 247 days.

(21) Appl. No.: 10/096,421

(22) Filed: Mar. 12, 2002

(65) Prior Publication Data
US 2003/0225069 A1 Dec. 4, 2003

(51) Int. Cl.⁷ ................... A61K 31/435; A61K 31/542; C07D 495/12; C07D 498/14

(52) U.S. Cl. ............. 514/287; 514/248; 514/224.2; 546/64; 546/63; 544/233; 544/247; 548/358.5

(58) Field of Search .................. 514/287, 248, 514/224.2; 546/64, 63; 544/233, 247; 548/358.5

(56) References Cited

U.S. PATENT DOCUMENTS

| | | | |
|---|---|---|---|
| 3,505,341 A | | 4/1970 | Elslager et al. |
| 3,963,740 A | | 6/1976 | Elslager |
| 4,026,899 A | | 5/1977 | Elslager |
| 4,539,412 A | | 9/1985 | Archer |
| 5,346,917 A | | 9/1994 | Miller et al. |
| 5,380,749 A | | 1/1995 | Miller et al. |
| 5,532,263 A | | 7/1996 | Wentland et al. |
| 5,935,969 A | * | 8/1999 | Krapcho .............. 514/287 |
| 6,034,092 A | | 3/2000 | Menta et al. |

FOREIGN PATENT DOCUMENTS

| | | |
|---|---|---|
| EP | 0 127 389 A2 | 12/1984 |
| EP | 0 284 966 A1 | 10/1988 |
| WO | WO 92/15300 | 9/1992 |
| WO | WO 94/06795 | 3/1994 |
| WO | WO 97/02267 | 1/1997 |
| WO | WO 98/49172 | 11/1998 |

OTHER PUBLICATIONS

Taylor et al., "3–Methyl–4–Nitropyridine–1–Oxide," *Org. Synth.* 4:654–656 (1963).

Watanabe et al., "Regioselective Syntheses of Substituted Thioxanthen– and Selenoxanthen–9–one Derivatives," *Chem. Pharm. Bull.* 37(1):36–41 (1989).

Yarinsky et al., "A Comparison of Molluscicidal and Molluse Inhibitory Activity of Hycanthone and Lucanthone and the Effect of the Drugs on the Development of *Schistosoma mansoni* in the Snail Intermediate Host, *Australorbis glabratus*," *J. Trop. Med. & Hyg.* 73:23–27 (1970).

Zee–Cheng et al., "Antineoplastic Agents. Structure–Activity Relationship Study of Bis(substituted aminoalkylamino)anthraquinones," *J. Med. Chem.* 21(3):291–294 (1978).

Crum et al., "The Chemistry of Heterocycles. IV. 2H–Pyrido [4,3–e]–1,3–oxazine–2,4[3H]–dione, Its Precursors and Some 3–Substituted Derivatives. (1–3)," *J. Heterocycl. Chem.* 3:252–256 (1966).

Gordon et al., "Antimuscarinic Activities of Hycanthone Analogs: Possible Relationship with Animal Toxicity," *J. Pharm. & Exp. Ther.* 236(1):85–89 (1986).

Haider et al., "Pyridazine Chemistry. Part 33. 5–Aminopyridazia–4–yl o–Fluorophenyl Ketone as a Key Intermediate in the Syntheses of Diaza Analogues of Acridone, Xanthone, and Thioxanthone," *J. Chem. Soc. Perkin Trans. I* 401–405 (1988).

Krapcho et al., "Synthesis and Antitumor Activities of 5–Methyl–1 and 2–[[2–Dimethylaminoethyl]amino]–Aza–Thiopyranoindazoles," *Bioorg. & Med. Chem. Letters* 10:305–308 (2000).

Palmer et al., "Potential Antitumor Agents. 54. Chromophore Requirements for In Vivo Antitumor Activity Among the General Class of Linear Tricyclic Carboxamides," *J. Med. Chem.* 31(4):707–712 (1988).

Ross, W.C.J., "The Preparation of Some 4–Substituted Nicotinic Acids and Nicotin–amides," *J. Chem. Soc.* (c):1816–1821 (1966).

Showalter et al., "Benzothiopyranoindazoles, A New Class of Chromophore Modified Anthracenedione Anticancer Agents. Synthesis and Activity Against Murine Leukemias," *J. Med. Chem.* 31(8):1527–1539 (1988).

Späth et al., "Die Synthese des Ricinins," *Chem. Ber.* 56:2454–2460 (1923) (German language).

Taylor et al., "Pyridine–1–Oxides, 1. Synthesis of Some Nicotinic Acid Derivatives," *J. Org. Chem.* 19:1633–1640 (1955).

Archer et al., "Electrophilic Aromatic Substitution, Part 34, Partial Rate Factors for Detritiation of Dithieno [1,2–b:4, 3–b']benzene, Dithieno[1,2–b:3,4–b']benzene, and Dithieno [2,1–b:3,4–b']benzene," *J. Chem. Soc. Perkin Trans. II* 813–819 (1983).

Arduengo et al., "Imidazolylidenes, Imidazolinylidenes and Imidazolidines," *Tetrahedron* 55:14523–14534 (1999).

Bailly et al., "Preferential Intercalation at AT Sequences in DNA by Lucanthone, Hycanthone, and Indazole Analogs. A Footprinting Study," *Biochem.* 32:5985–5993 (1993).

Beylin et al., "An Improved Synthesis of Anticancer Benzothiopyranoindazoles. An Efficient Large–Scale β–Aminoethylation Procedure [1]," *J. Heterocyclic Chem.* 28:517–527 (1991).

(List continued on next page.)

Primary Examiner—Samuel Barts
Assistant Examiner—Michael C. Henry
(74) Attorney, Agent, or Firm—Nixon Peabody LLP

(57) ABSTRACT

The present invention relates to a group of aza-anthrapyrazole compounds having antitumor activity, and processes for their preparation. Compositions containing the aza-anthrapyrazole compounds and methods of treating tumors and cancer in mammals with the compounds of the present invention are also disclosed.

52 Claims, No Drawings

OTHER PUBLICATIONS

Blanz et al., "A Systematic Investigation of Thioxanthen–9–ones and Analogs as Potential Antitumor Agents," *J. Med. Chem.* 6:185–191 (1963).

Cheng et al., "The Design, Synthesis and Development of a New Class of Potent Antineoplastic Anthraquinones," *Progress in Medicinal Chemistry*, Ellis and West, eds. Amsterdam: Elsevier, 20:83–118 (1983).

Coe et al., "Synthesis and Antiviral Properties of Some 2'–Deoxy–5–(fluoroalkenyl) Uridines," *J. Med. Chem.* 25:1329–1334 (1982).

Croisy–Delcey et al., "Aza Analogues of Lucanthone: Synthesis and Antitumor and Bactericidal Properties," *J. Med. Chem.* 26(9):1329–1333 (1983).

* cited by examiner

AZA-BENZOTHIOPYRANOINDAZOLES WITH ANTITUMOR ACTIVITY

FIELD OF THE INVENTION

The present invention relates to a group of aza-benzothiopyranoindazole compounds having antitumor activity, and processes for their preparation.

BACKGROUND OF THE INVENTION

Cellular Proliferation and Cancer.

The disruption of external or internal regulation of cellular growth can lead to uncontrolled proliferation and in cancer, tumor formation. This loss of control can occur at many levels and, indeed, does occur at multiple levels in most tumors. Further, although tumor cells can no longer control their own proliferation, they still must use the same basic cellular machinery employed by normal cells to drive their growth and replication.

Aza-Benzothiopyranoindazoles Antitumor Agents.

Certain 1,4-bis[(aminoalkyl)amino]anthracene-9,10-diones have been reported which show antitumor activity in clinical trials. Of particular interest has been ametantrone, 1,4-bis[(2-(2-hydroxyethylamino)ethyl)amino]anthracene-9,10-dione and mitoxantrone, 5,8-dihydroxy-1,4-bis[(2-(2-hydroxyethylamino)ethyl)amino]anthracene-9,10-dione (Zee-Cheng et al., "Antineoplastic Agents. Structure-Activity Relationship Study of Bis(substituted aminoalkylamino)anthraquinones," $J.$ $Med.$ $Chem.$ 21:291–294 (1978); and Cheng et al., "Progress in Medicinal Chemistry", Ellis, G. P. and West, G. B., Elsevier: Amsterdam, vol. 202, p. 83 (1983)).

Mitoxantrone is a broad-spectrum oncolytic agent, whose activity is similar to that of the anthracyclines antibiotic doxorubicin. Clinical trials have demonstrated a diminish cardiotoxicity in comparison to doxorubicin. Both mitoxantrone and ametantrone have remarkable myelodepressive toxicity and both compounds show cross-resistance to cell histotypes developing resistance against doxorubicin mediated by overexpression of glycoprotein P (also known as multidrug resistance).

In an attempt to overcome the above-mentioned drawbacks, some chromophore modified anthracendiones have been reported.

Blanz et al., $J.$ $Med.$ $Chem.$ 6:185–191 (1963) discloses the synthesis of a series of thioxanthenones related to lucanthones and the results of the testing of the compounds against leukemia and two solid tumors. Among the compounds disclosed are:

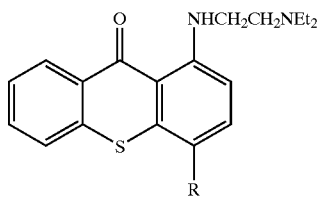

where R is methyl, methoxyl, and ethoxyl.

Yarinsky et al., $J.$ $Trop.$ $Med.$ $\&$ $Hyg.$ 73:23–27 (1970) discloses

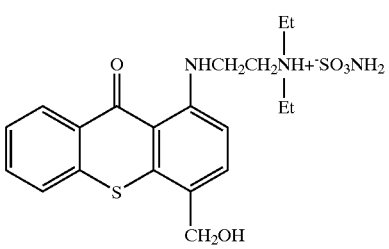

as an antischistosomal agent.

Palmer et al., "Potential Antitumor Agents. 54. Chromophore Requirements for in vivo Antitumor Activity Among the General Class of Linear Tricyclic Carboxamides," $J.$ $Med.$ $Chem.$ 31(4):707–712 (1988) discloses N-[2-(dimethylamino)ethyl-]-9-oxo-9H-thioxanthene-4-carboxamide monohydrochloride which was tested in vitro versus murine leukemia (L1210) and in vivo versus P388 leukemia cells and was found to be "unlikely to worth pursuing" as a potential antitumor agent.

U.S. Pat. No. 4,539,412 to Archer discloses compounds of the formula:

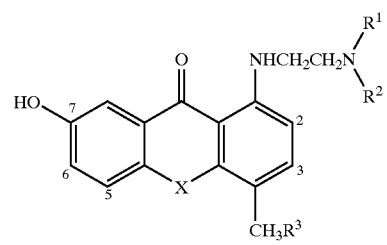

where for X=S: $R^1$ and $R^2$ are individually selected from one of lower-alkyls, and jointly selected from one of pyrolidinyl, piperidinyl, morpholinyl, piperazinyl and N-substituted piperazinyl; and $R^3$ is hydroxy. The compounds are said to be useful as antitumor agents.

However, the search for newer active analogues is still highly desirable. WO 94/06795 describes aza-thiopyranopyridine derivatives which are endowed with antitumor activity. WO 98/49172 to Krapcho discloses compounds of the formula:

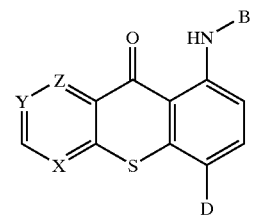

where one of X, Y, or T is nitrogen (=N—) and the others are =CH—; D is selected from the group consisting of $C_1$–$C_4$ alkyl, nitro or —NH—A, where A is on its turn is selected from the group consisting of hydrogen, —CO—, $CH_2$—$NR_2R_3$ and alkyl. B is selected in the group consisting of $C_1$–$C_{10}$ alkyl having one or two substituents selected from the group consisting of $OR_1$ and —$NR_2R_3$. These compounds have antitumor activity against human leukemias and solid tumors sensitive to treatment with mitoxantrone and antitumor antibiotics, such as doxorubicin.

Aza-derivatives of lucanthone have also been described. For example, M. Croisy-Delcey et al., "Aza Analogues of Lucanthone: Synthesis and Antitumor and Bactericidal Properties," $J.$ $Med.$ $Chem.$ 26(9):1329–1333 (1983) and Blanz et al., $J.$ $Med.$ $Chem.$ 6:185–191 (1963) describe the following compounds, respectively:

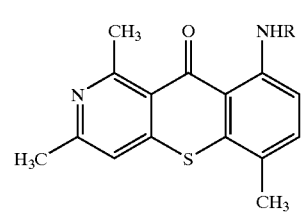

(1)

-continued

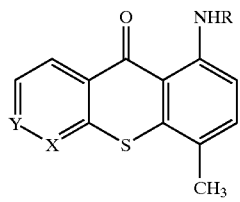

(2)

where R is an aminoalkyl chain and, in (2), one of X or Y is nitrogen and the other is carbon. In both the cases these compounds showed little, if any, antitumor activity.

U.S. Pat. No. 5,346,917 to Miller et al. discloses compounds of the formula:

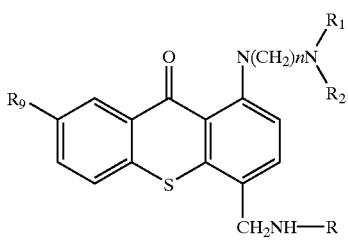

where n is 2 or 3; R is hydrogen, C(O)H, C(O)R$_3$, SO$_2$R$_3$ and C(O)OR$_3$; R$_1$ and R$_2$ are independently hydrogen or lower alkyl; and R$_9$ is hydrogen, lower-alkyl; lower-alkoxy, or hydroxy.

In addition, European Patent Application No. 127,389 to Elslager et al. discloses N,N, diethyl-5-methyl-2H-[1]-benzothiopyrano[4,3,2-cd]indazole-2-ethanamine which is stated to be useful as an antitumor agent.

European Patent Application No. 284,966 to Beylin et al. discloses a process for preparing compounds of the formula:

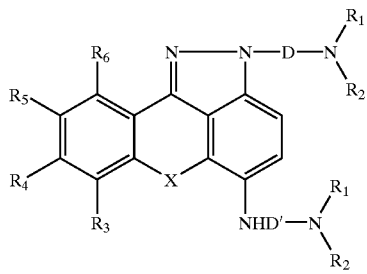

where X is oxygen, sulfur or selenium; D and D' may be the same or different and are a straight or branched alkylene group of from two to five carbon atoms; R$_1$ and R$_2$ may be the same or different and are hydrogen or an alkyl group of from two to eight carbon atoms which may be substituted by hydroxy; R$_3$, R$_4$, R$_5$ and R$_6$ may be the same or different and are hydrogen or hydroxy; or a pharmaceutically acceptable salt thereof. The compounds are stated to possess antibacterial, antifungal and antineoplastic activity. A similar disclosure is found in Beylin et al., *J. Heterocyclic Chem.* 28:517–527 (1991).

U.S. Pat. No. 3,505,341 to Elslager et al. discloses compounds of the formula:

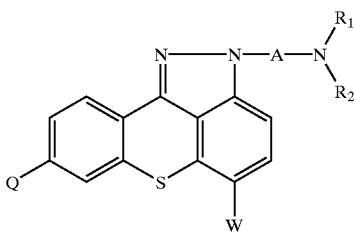

where A is an alkylene radical containing 2 to 4 carbon atoms; Q is a hydrogen or halogen atom; R$_1$ and R$_2$ are the same or different and represent C$_1$–C$_4$ alkyl or together with the nitrogen atom [—N(R$_1$)R$_2$] a lower alkylene radical containing 4 to 8 carbon atoms, 4 to 6 of which are joined in a ring with the nitrogen atom; and W is the aldehyde group —CHO or a methyl or hydroxymethyl group. The compounds are stated to possess antiparasitic and antibacterial activity.

U.S. Pat. No. 3,963,740 to Elslager discloses compounds of the formula:

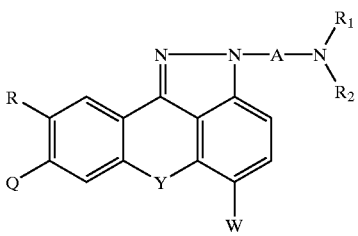

where A is an alkylene radical containing 2 to 4 carbon atoms. R$_1$ and R$_2$ are the same or different and represent C$_1$–C$_4$ alkyl or together a lower-alkylene radical containing 4 to 8 carbon atoms, 4 to 6 of which are joined in ring with the nitrogen atom; and W is methyl, hydroxymethyl, or acyloxymethyl where said acyl fragment contains from one to eight carbon atoms; Y is S or O; and one of Q and R is hydrogen and the other is selected from hydrogen and a substituted halo or alkoxy group having one to four carbon atoms. The compounds are stated to be intermediates in the preparation of the corresponding N-oxide derivative which are stated to be useful as parasiticidal agents. A similar disclosure is found in U.S. Pat. No. 4,026,899 to Elslager.

Blanz et al., *J. Med. Chem.* 6:185–191 (1963) discloses 5-methyl-2H-[1]benzothiopyrano[4,3,2-cd]indazole (example 39) which was tested and found to be inactive as an antitumor agent.

Showalter et al., "Benzothiopyranoindazoles, A New Class of Chromophore Modified Anthracenedione Anticancer Agents. Synthesis and Activity Against Murine Leukemias," *J. Med. Chem.* 31(8):1527–1538 (1988) discloses the synthesis and anticancer activity of a series of substituted 5-amino-2H-[1]benzothiopyrano[4,3,2-cd]indazol2-2-ethanamine.

Baily et al., *Biochem.* 32:5985–5993 (1993) discloses compounds of the formula:

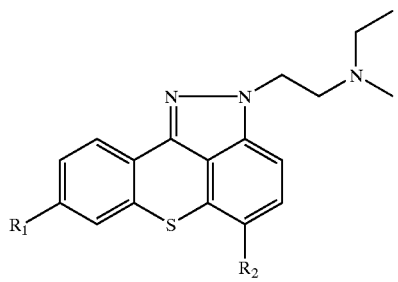

where $R_1$=Cl and $R_2$=$CH_3$; $R_1$=Cl and $R_2$=$CH_2OH$. The compounds are stated to exhibit antitumor activity.

Gordon et al., "Antimuscarinic Activities of Hycanthone Analogs: Possible Relationship with Animal Toxicity," *J. Pharm. & Exp. Ther.* 236(1):85–89 (1986) discloses N,N-diethyl-5-methyl-8-chloro-2H-[1]benzothiopyrano-[4,3,2-cd] indazole-2-ethanamine and their testing for antimuscarinic activity.

WO 94/06795 describes aza-benzothiopyranoindazole derivatives which are endowed with antitumor activity. U.S. Pat. No. 5,935,969 to Krapcho discloses compounds of the formula:

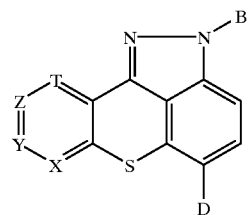

where one of X, Y, Z, or T is nitrogen (=N—) and the others are =CH—; D is selected from the group consisting of nitro or —NH—A, where A is on its turn is selected from the group consisting of hydrogen, —CO—, $CH_2$—$NR_2R_3$ or alkyl. B is selected in the group consisting of $C_1$–$C_{10}$ alkyl having one or two substituents selected from the group consisting of OR, and —$NR_2R_3$.

U.S. Pat. No. 5,532,263 to Wentland et al. discloses compounds of the formula:

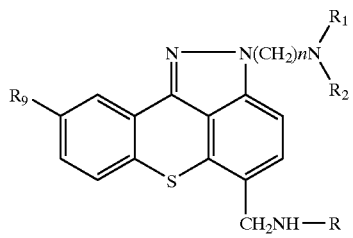

where n is 2 or 3; R is hydrogen, C(O)H, $C(O)R_3$, $SO_2R_3$ and $C(O)OR_3$; $R_1$ and $R_2$ are independently hydrogen or lower alkyl; and $R_9$ is hydrogen, lower-alkyl; lower-alkoxy, or hydroxy.

The present invention is directed to overcoming these deficiencies in the art.

SUMMARY OF THE INVENTION

The present invention is directed to a compound of the following formula:

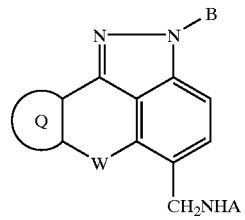

where:
W is selected from the group consisting of S, SO, and $SO_2$;
Q is a 5- or 6-membered aromatic ring having at least one atom selected from the group consisting of N and S;
A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H; $C(O)OR_1$; $SO_2R_1$; $(CH_2)_nNH(CH_2)_mCH_3$; $(CH_2)_nN((CH_2)_mCH_3)(CH_2)_pCH_3$; and $(CH_2)_nD$;
B is selected in the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; $(CH_2)_nNH(CH_2)_mCH_3$; $(CH_2)_nN((CH_2)_mCH_3)(CH_2)_pCH_3$; and $(CH_2)_nD$;
$R_1$ is selected from a group consisting of $C_1$–$C_{10}$alkyl, phenyl, and phenyl alkyl, as free bases;
n is 2–3;
m is 0–3;
p is 0–3; and
D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom or
pharmaceutically acceptable salts.

Another aspect of the present invention is directed to a process for preparation of a product compound of the formula:

(II)

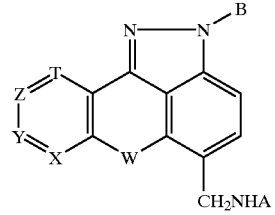

where:
one or more of X, Y, Z, or T=N;
W is selected from the group consisting of S, SO, and $SO_2$;
A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy;

C(O)H, C(O)OR$_1$, SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;

B is selected from the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;

R$_1$ is selected from a group consisting of C$_1$–C$_{10}$ alkyl, phenyl, and phenyl alkyl, as free bases;

n is 2–3;

m is 0–3;

p is 0–3; and

D is selected from the group consisting of: hydroxy; C$_1$–C$_4$ linear or branched alkoxy which is substituted or unsubstituted; and a 5- or 6-member aromatic or non-aromatic heterocyclic ring containing a sulfur, oxygen, or nitrogen heteroatom; or pharmaceutically acceptable salts thereof, said process comprising:
transforming a first intermediate compound of the formula:

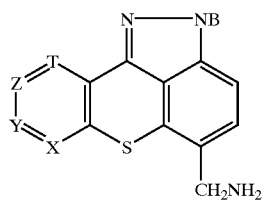

under conditions effective to form the product compound.

The present invention is also directed to a process for preparation of a product compound of the formula:

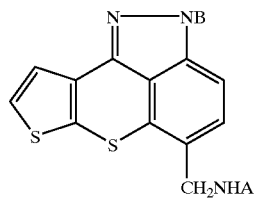

where:
A is selected from the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; C(O)H; C(O)OR$_1$; SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;

B is selected in the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; (CH$_2$)$_n$NH (CH$_2$)$_m$CH$_3$; (CH$_2$)$_n$N((CH$_2$)$_m$CH$_3$)(CH$_2$)$_p$CH$_3$; and (CH$_2$)$_n$D;

R$_1$ is selected from a group consisting of C$_1$–C$_{10}$ alkyl, phenyl, and phenyl alkyl, as free bases;

n is 2–3;

m is 0–3;

p is 0–3; and

D is selected from the group consisting of: hydroxy; C$_1$–C$_4$ linear or branched alkoxy which is substituted or unsubstituted; and a 5- or 6-member aromatic or non-aromatic heterocyclic ring containing a sulfur, oxygen, or nitrogen heteroatom; or a pharmaceutically acceptable salt thereof, said process comprising:
transforming a first intermediate compound of the formula:

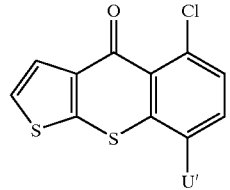

wherein U'=H, F, Cl, Br or I, under conditions effective to form the product compound.

The present invention is also directed to a process for preparation of a product compound of the formula:

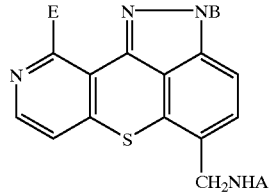

where:
A is selected from the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; C(O)H; C(O)OR$_1$; SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;

B is selected in the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; (CH$_2$)$_n$NH (CH$_2$)$_m$CH$_3$; (CH$_2$)$_n$N((CH$_2$)$_m$CH$_3$)(CH$_2$)$_p$CH$_3$; and (CH$_2$)$_n$D;

R$_1$ is selected from a group consisting of C$_1$–C$_{10}$ alkyl, phenyl, and phenyl alkyl, as free bases;

n is 2–3;

m is 0–3;

p is 0–3;

E is OCH$_3$ or Cl; and

D is selected from the group consisting of: hydroxy; C$_1$–C$_4$ linear or branched alkoxy which is substituted or unsubstituted; and a 5- or 6-member aromatic or non-aromatic heterocyclic ring containing a sulfur, oxygen, or nitrogen heteroatom; or a pharmaceutically acceptable salt thereof, said process comprising:
transforming a first intermediate compound of the formula:

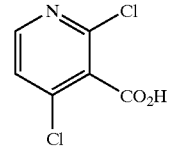

under conditions effective to form the product compound.

The present invention is also directed to a method for inhibiting cell proliferation in mammals. This method involves administering to a mammal a therapeutically effective amount of the compound of the following formula, and as described above:

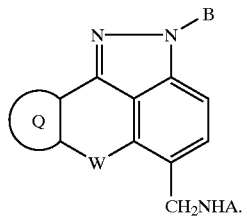

The present invention is also directed to a pharmaceutical composition of matter including the following compound and one or more pharmaceutical excipients:

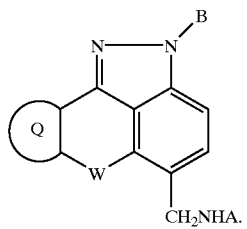

DETAILED DESCRIPTION OF THE INVENTION

The present invention is directed to a compound of the following formula (I):

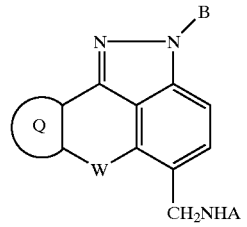

where:

W is selected from the group consisting of S, SO, and $SO_2$;

Q is a 5- or 6-membered aromatic ring having at least one atom selected from the group consisting of N and S;

A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H; C(O)$OR_1$; $SO_2R_1$; $(CH_2)_nNH(CH_2)_mCH_3$; $(CH_2)_nN((CH_2)_mCH_3)(CH_2)_pCH_3$; and $(CH_2)_nD$;

B is selected in the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; $(CH_2)_nNH(CH_2)_mCH_3$; $(CH_2)_nN((CH_2)_mCH_3)(CH_2)_pCH_3$; and $(CH_2)_nD$;

$R_1$ is selected from a group consisting of $C_1$–$C_{10}$ alkyl, phenyl, and phenyl alkyl, as free bases;

n is 2–3;

m is 0–3;

p is 0–3; and

D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom or pharmaceutically acceptable salts.

A preferred form of the compound of the present invention has the following formula (II):

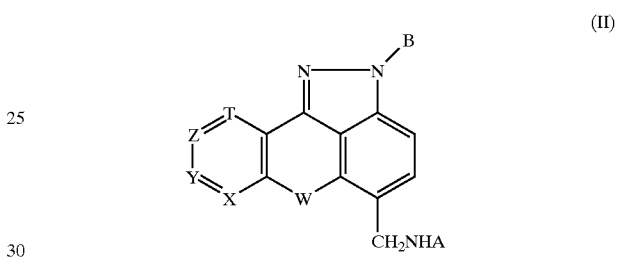

where:

one or more of X, Y, Z, or T=N;

W is selected from the group consisting of S, SO, and $SO_2$;

A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H, C(O)$OR_1$, $SO_2R_1$; $(CH_2)_nNH(CH_2)_mCH_3$; $(CH_2)_nN((CH_2)_mCH_3)(CH_2)_pCH_3$; and $(CH_2)_nD$;

B is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; $(CH_2)_nNH(CH_2)_mCH_3$; $(CH_2)_nN((CH_2)_mCH_3)(CH_2)_pCH_3$; and $(CH_2)_nD$;

$R_1$ is selected from a group consisting of $C_1$–$C_{10}$ alkyl, phenyl, and phenyl alkyl, as free bases;

n is 2–3;

m is 0–3;

p is 0–3; and

D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom; or pharmaceutically acceptable salts thereof.

Examples of the class of compounds according to formula (II) are set forth in Table 1.

TABLE 1

Compounds of Formula (II)

| X | Y | Z | T | Structure | Name of the Heterocyclic System |
|---|---|---|---|---|---|
| N | CH | CH | CH | (structure) | 2H-6-thia-1,2,7-triaza-aceanthrylen-5-yl)-alkylamine |
| CH | N | CH | CH | (structure) | 2H-6-thia-1,2,8-triaza-aceanthrylen-5-yl)-alkylamine |
| CH | CH | N | CH | (structure) | 2H-6-thia-1,2,9-triaza-aceanthrylen-5-yl)-alkylamine |
| CH | CH | CH | N | (structure) | 2H-6-thia-1,2,10-triaza-aceanthrylen-5-yl)-alkylamine |

Examples of preferred compounds of formula (II) are described in Table 2, below.

TABLE 2

Preferred Compounds of Formula (II)

| COMPOUND | Name of Heterocyclic System |
|---|---|
| (structure with CH$_2$NHCHO) | N-[2-(2-Diethylamino-ethyl)-2H-6-thia-1,2,9-triaza-aceanthrylen-5-ylmethyl]-formamide |
| (structure with CH$_2$NH$_2$) | [2-(5-Aminomethyl)-6-thia-1,2,9-triaza-aceanthrylen-2-yl)-ethyl]-diethyl-amine |

TABLE 2-continued

Preferred Compounds of Formula (II)

| COMPOUND | Name of Heterocyclic System |
|---|---|
| (structure with CH₂NHCO₂CH₃ substituent) | [2-(2-Diethylamino-ethyl)-2H-6-thia-1,2,9-triaza-aceanthrylen-5-ylmethyl]-carbamic acid methyl ester |
| (structure with CH₂NHSO₂CH₃ substituent) | N-[2-(2-Diethylamino-ethyl)-2H-6-thia-1,2,9-triaza-aceanthrylen-5-ylmethyl]-methanesulfonamide |
| (structure with CH₂NHCHO substituent) | N-[2-(2-Diethylamino-ethyl)-2H-6-thia-1,2,7-triaza-aceanthrylen-5-ylmethyl]-formamide |
| (structure with CH₂NH₂ substituent) | [2-(5-Aminomethyl)-6-thia-1,2,7-triaza-aceanthrylen-2-yl)-ethyl]-diethyl-amine |
| (structure with CH₂NHCO₂CH₃ substituent) | [2-(2-Diethylamino-ethyl)-2H-6-thia-1,2,7-triaza-aceanthrylen-5-ylmethyl]-carbamic acid methyl ester |

TABLE 2-continued

Preferred Compounds of Formula (II)

| COMPOUND | Name of Heterocyclic System |
|---|---|
| [structure with CH₂NHSO₂CH₃ substituent] | N-[2-(2-Diethylamino-ethyl)-2H-6-thia-1,2,7-triaza-aceanthrylen-5-ylmethyl]-methanesulfonamide |
| [structure with CH₂NHCHO substituent] | N-[2-(2-Diethylamino-ethyl)-2H-6-thia-1,2,8-triaza-aceanthrylen-5-ylmethyl]-formamide |
| [structure with CH₂NH₂ substituent] | [2-(5-Aminomethyl)-6-thia-1,2,8-triaza-aceanthrylen-2-yl)-ethyl]-diethyl-amine |
| [structure with CH₂NHCO₂CH₃ substituent] | [2-(2-Diethylamino-ethyl)-2H-6-thia-1,2,8-triaza-aceanthrylen-5-ylmethyl]-carbamic acid methyl ester |

TABLE 2-continued

Preferred Compounds of Formula (II)

| COMPOUND | Name of Heterocyclic System |
|---|---|
| (structure with CH₂NHSO₂CH₃) | N-[2-(2-Diethylamino-ethyl)-2H-6-thia-1,2,8-triaza-aceanthrylen-5-ylmethyl]-methanesulfonamide |
| (structure with CH₂NHCHO) | N-[2-(2-Diethylamino-ethyl)-2H-6-thia-1,2,10-triaza-aceanthrylen-5-ylmethyl]-formamide |
| (structure with CH₂NH₂) | [2-(5-Aminomethyl)-6-thia-1,2,10-triaza-aceanthrylen-2-yl)-ethyl]-diethyl-amine |
| (structure with CH₂NHCO₂CH₃) | [2-(2-Diethylamino-ethyl)-2H-6-thia-1,2,10-triaza-aceanthrylen-5-ylmethyl]-carbamic acid methyl ester |

TABLE 2-continued

Preferred Compounds of Formula (II)

| COMPOUND | Name of Heterocyclic System |
|---|---|
| (structure with CH₂NHSO₂CH₃) | N-[2-(2-Diethylamino-ethyl)-2H-6-thia-1,2,10-triaza-aceanthrylen-5-ylmethyl]-methanesulfonamide |

Synthetic Schemes for Preparation of the Compounds of Formula (II)

The compounds of formula (II) can be prepared by a number of synthetic schemes.

One example of such a scheme is that of Scheme 1 as follows:

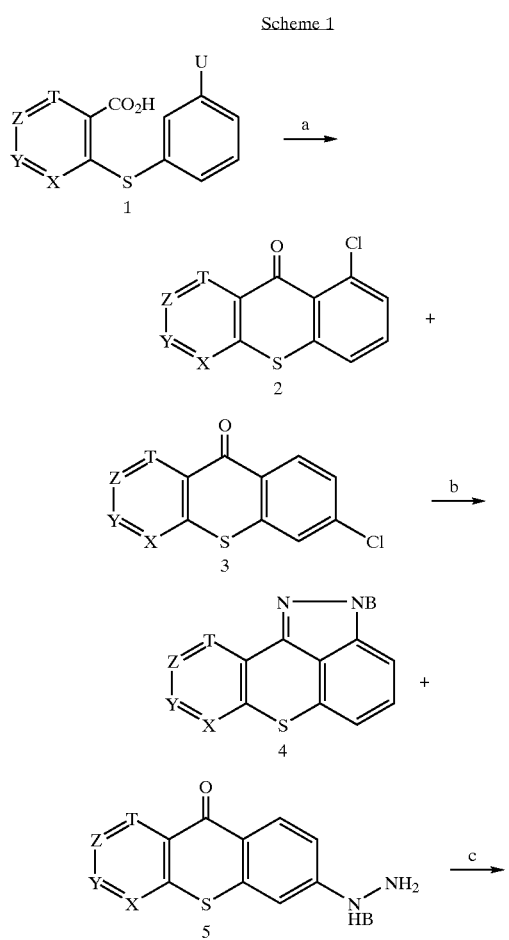

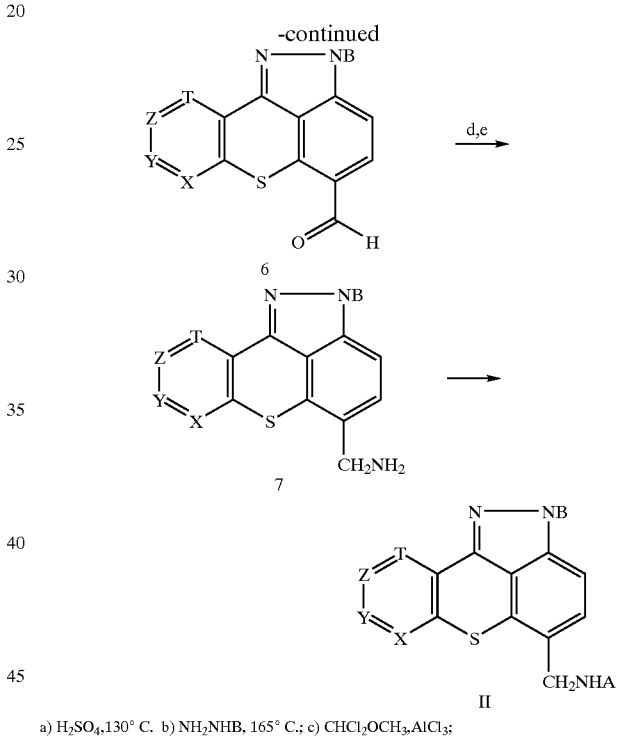

a) $H_2SO_4$, 130° C. b) $NH_2NHB$, 165° C.; c) $CHCl_2OCH_3$, $AlCl_3$;
d) $HCONH_2$, $HCO_2H$, 140° C.; e) 2 N NaOH, 100° C.

Cyclization of compound 1, where X, Y, Z, and T are as above defined and where U is Cl, can be accomplished with concentrated sulfuric acid at 130° C. to give a mixture of isomers compounds 2 and 3. Next, condensation of the mixture of compounds 2 and 3 with $NH_2NHB$ at 165° C. can yield the desired product 4, which can be separated from the byproduct 5 by column chromatography. Reaction of compound 4 with $CHCl_2OCH_3$ and $AlCl_3$ can yield the desired aldehyde 6. The resulting intermediate can be reacted with formic acid and formamide (Leuckart Conditions) to provide the formamide intermediate. The latter compound can be hydrolyzed with 2 N NaOH to give the desired amine 7. Compound 7 can be converted to compounds of formula II using chemical transformations known to those skilled in the art.

Alternatively, compounds 2 and 3 can be prepared by cyclization of the compound 1 in which X, Y, Z, and T are as above defined and U is selected from the group consisting of F and Cl. This reaction can be performed using different methods known in the art, such as:

(i) Transforming the carboxylic acid moiety into an acyl chloride by reaction with thionyl chloride, for example, and, subsequently, performing a Friedel-Crafts reaction in the presence of a Lewis acid, such as aluminum trichloride, in a suitable solvent, such as nitrobenzene and at a temperature ranging from between 0° C. and 150° C.; and (ii) Cyclizing the compounds (3) in the presence of concentrated sulfuric acid at a temperature ranging from room temperature to 150° C.

Compounds of formula 4 and 5 can alternatively be prepared from the reaction of a mixture of compounds 2 and 3 with substituted hydrazine: $H_2N-NH-B'$, where B' is the same as B as defined in formula (II) above, or B' is a group that can be converted into B by removal of protective groups for the primary or secondary amines and hydroxy groups optionally present in B', to give compound 4. The reaction of compounds 2 and 3 with the substituted hydrazine can be done by reacting the mixture with at least a stoichiometric amount of the substituted hydrazine. The reaction is usually performed in an inert solvent such as methylene chloride, chloroform, 1,1,1-trichloroethane, dimethoxyethane, tetrahydrofuran, dimethylsulfoxide, dimethylformamide, pyridines and mixtures thereof, or if it is desired using the substituted hydrazine itself as the solvent.

As shown in Scheme 2, when X is nitrogen, compound 10 can be obtained by reacting 2-chloro-nicotinic acid (8) with 2,5-disubstituted thiophenol (9) in refluxing acetone as follows:

Scheme 2

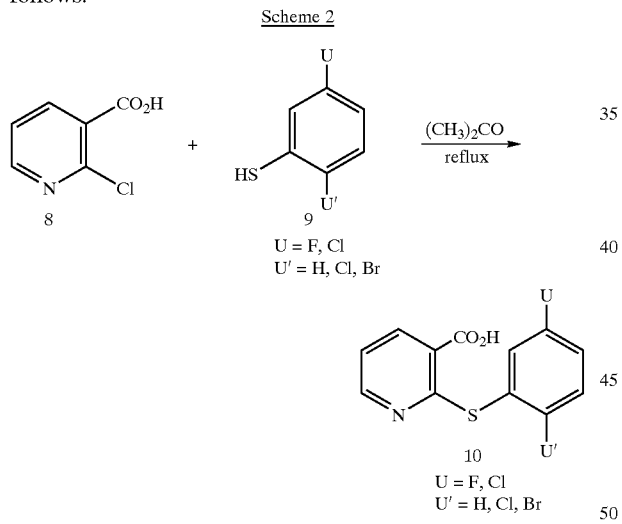

When Y is nitrogen, compound 12 can be obtained by reacting the dizonium salt of 3-amino-4-carboxylic acid pyridine (11) with the anion of 2,5-disubsituted thiophenol (9) in refluxing acetone as outlined in Scheme 3 below:

Scheme 3

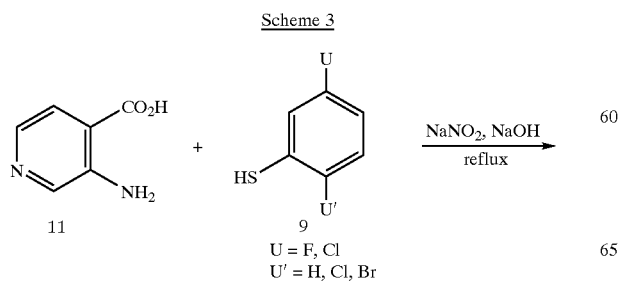

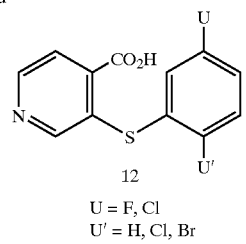

When Z is nitrogen, compound 14 can be obtained by reacting 4-chloronicotinic acid (13) and 2,5-disubstituted thiophenol (9) in a solvent at temperatures from room temperature up to the boiling point of the solvent. A preferred condition is to reflux the mixture of the two reactants in acetone as a solvent. This process for producing compound 14 may be carried out as depicted in Scheme 4 below:

Scheme 4

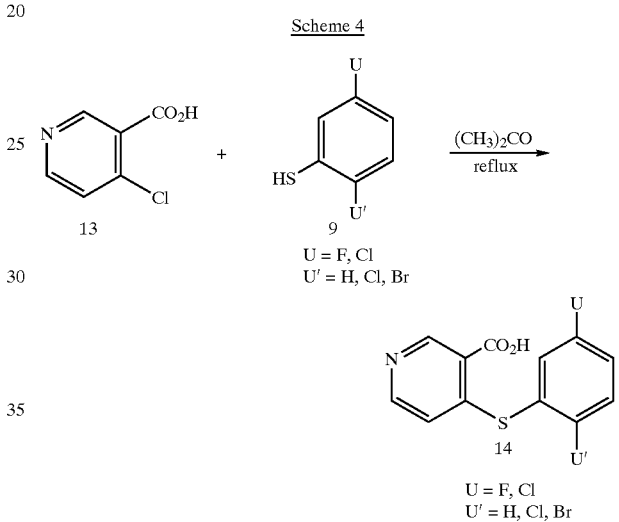

When T is nitrogen, compound 16 can be obtained by reacting the diazonium salt of 3-amino-2-carboxylic acid pyridine (15) with the anion of 2,5-disubstituted thiophenol (9) in refluxing acetone as depicted in Scheme 5 below:

Scheme 5

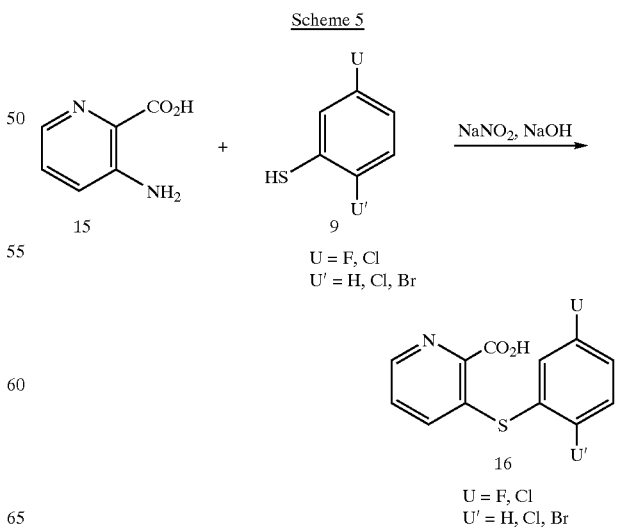

An alternative regioselective synthesis for compound 4 (where X=N or Z=N) is detailed in Scheme 6 below:

to give the desired product 4 (X=CH, Z=N). In the second route, compound 20 (X=CH, Z=N, U'=Cl or Br) is treated Scheme 6

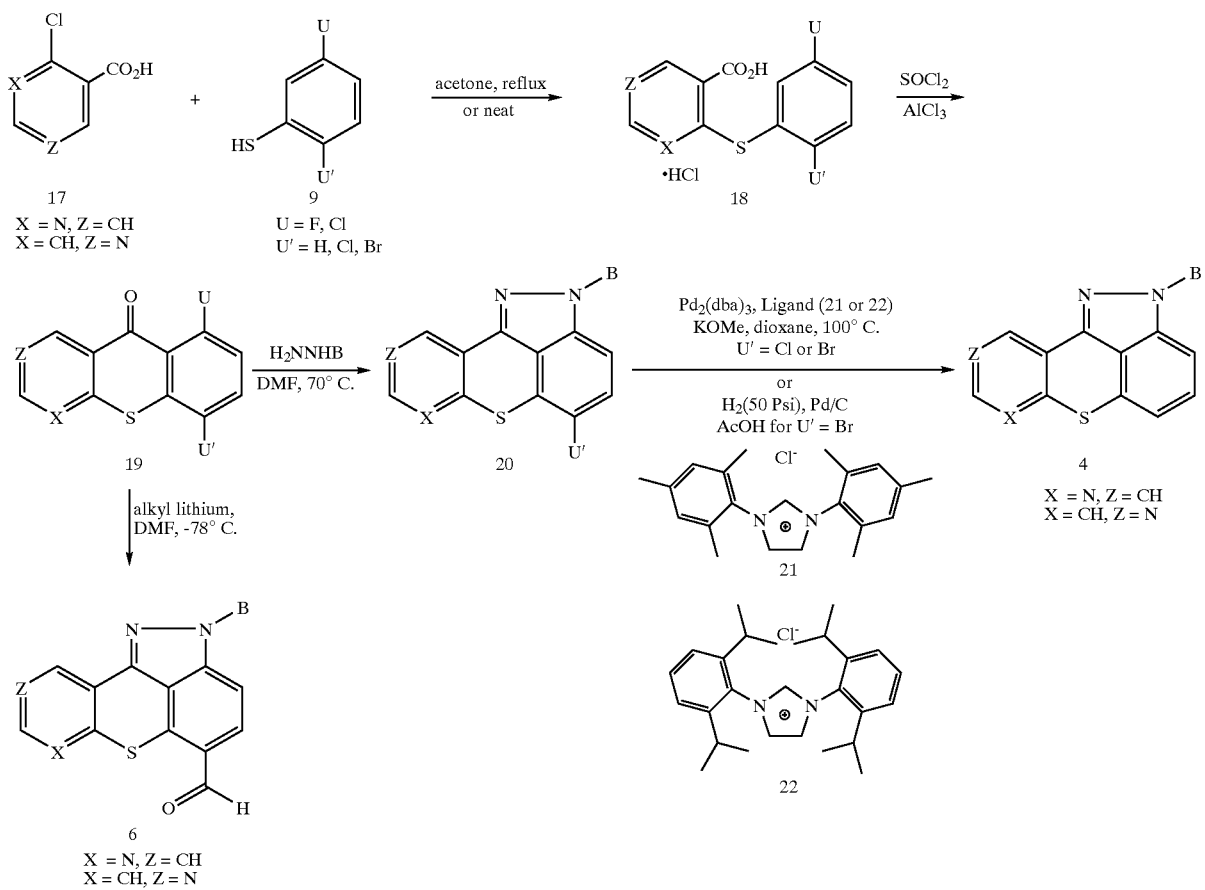

Ref: Arduengo III et. al., Tetrahedron 55:14523–14534 (1999), which is hereby incorporated by reference in its entirety.

As depicted in Scheme 6, 2-fluoro-5-bromothiophenol (9) is reacted with 4-chloro-3-carboxylic acid pyridine (17) (X=CH, Z=N) in refluxing acetone to yield compound 18 (X=CH, Z=N). Compound 18 is then converted to the acetyl chloride derivative which cyclized upon treatment with aluminium chloride to give compound 19 (X=CH, Z=N). Upon condensation of compound 19 with the appropriate substituted hydrazine in DMF at 70° C., the tetracyclic core 20 (X=CH, Z=N) is isolated. Compound 20 (X=CH, Z=N, U'=Cl or V=Br) is converted to compound 4 (X=CH, Z=N) via either two routes. In the first route, compound 20 is reacted with alkyl lithium, followed with quenching the reaction with dimethylformamide at −78° C.

with Pd (O) and the appropriate ligand (21 or 22, which can be prepared according to Arduengo III et al., *Tetrahedron* 55:14523–14534 (1999), which is hereby incorporated by reference in its entirety) to give compound 4 (X=CH, Z=N). Alternatively, when U'=Br, compound 4 (X=CH, Z=N) can be obtained by reductive debromination of compound 20 using Pd/C and $H_{2(g)}$. Using a similar approach, the aza series where X=N, Z=CH can be constructed from 2-chloro-3-carboxylic acid pyridine (17) (X=N, Z=CH) (Scheme 6, above).

An alternative regioselective synthesis for compound 4 (where Y=N or T=N) is depicted in Scheme 7 below.

Scheme 7

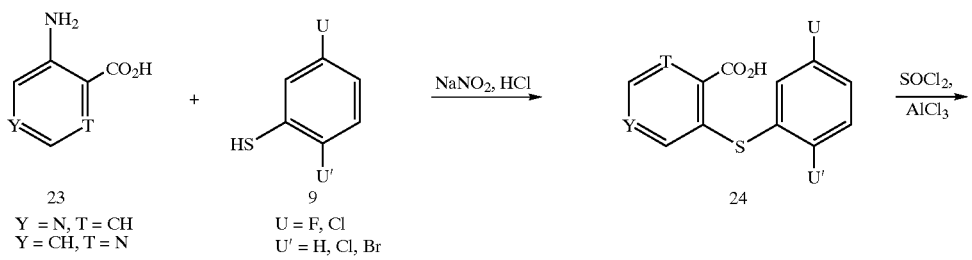

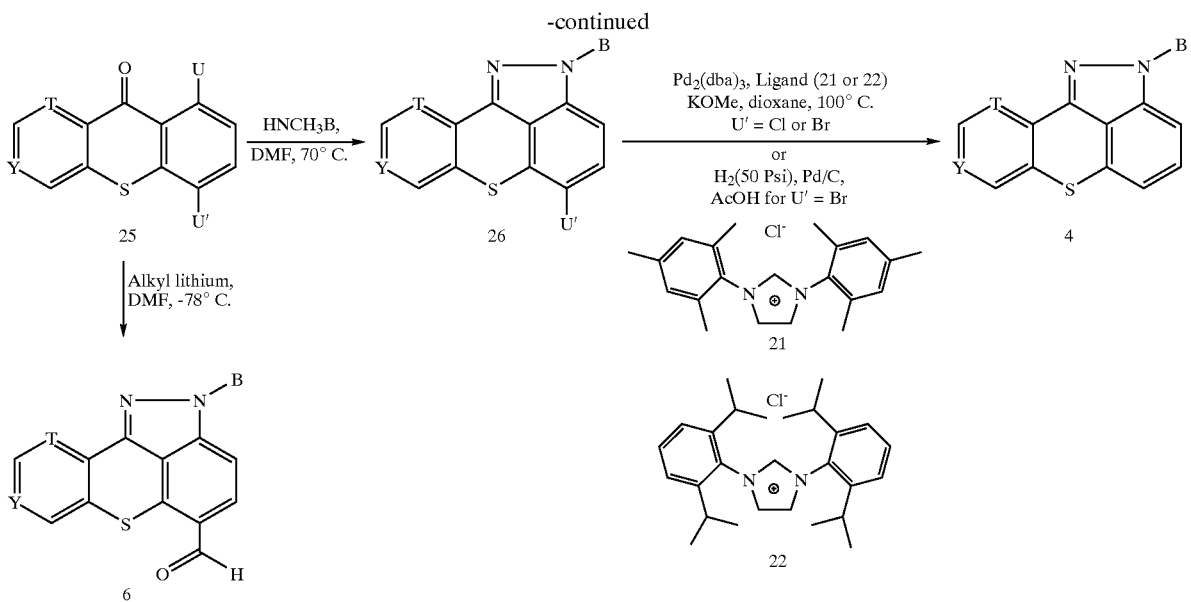

Ref: Arduengo III et. al., Tetrahedron 55:14523–14534 (1999), which is hereby incorporated by reference in its entirety.

As for the aza series (Scheme 7) where Y=N, T=CH or Y=CH, T=N, the corresponding compound 4 (Y=N, or T=N) can be derived from multisteps synthesis starting from the corresponding amines (23) where Y=N, T=CH or Y=CH, T=N, respectively, using a sequence of synthetic steps described above, and as described in Scheme 7, above.

As depicted in Scheme 8 (below), compound 9 (U=F, U'=Br) can be synthesized in three steps from commercially available material, including, for example, from 2-bromo-5-fluoro-phenol (27). Hence, reaction of compound 27 with N-N-dimethylthiocarbamoyl chloride in the presence of NaH in DMF, yields compound 28. Heating compound 28 in diphenyl ether at 260° C. results in Newmann-Kwart rearrangement to give compound 29. Upon reaction with potassium hydroxide in methanol followed by an acidic workup, compound 29 yields the desired compound 9.

Scheme 8

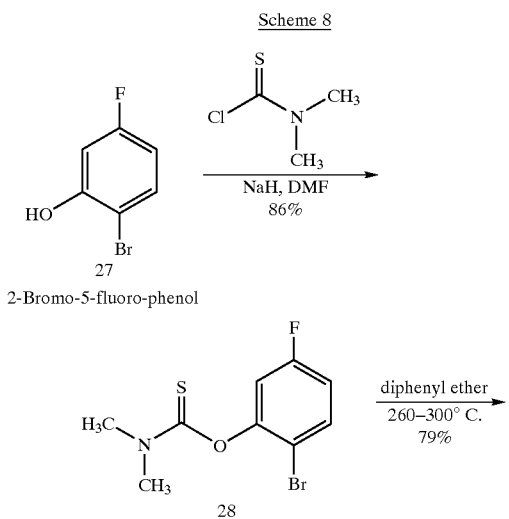

Synthesis of a specific 2-Aza acid intermediate (11) used in Scheme 3 of the present invention is shown below as Scheme 9:

Scheme 9

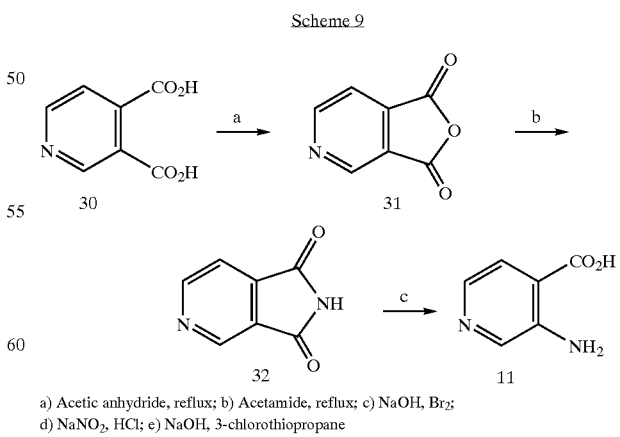

a) Acetic anhydride, reflux; b) Acetamide, reflux; c) NaOH, Br$_2$; d) NaNO$_2$, HCl; e) NaOH, 3-chlorothiopropane Ref: Crum et al., J. Heterocycl. Chem. 3:252 (1966), which is hereby incorporated by reference in is entirety.

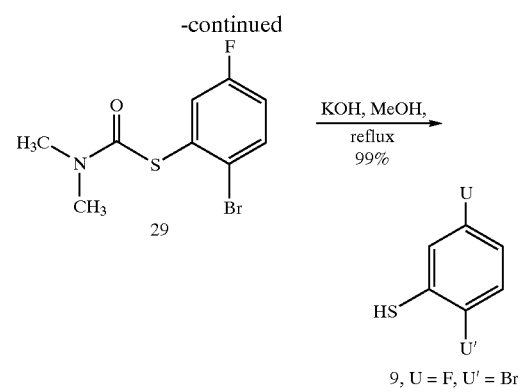

As depicted in Scheme 9, above, the commercially available pyridine-3,4-dicarboxylic acid (30) can be treated with acetic anhydride to give cinchonomeric anhydride (31). Upon treatment of anhydride 31 with acetamide, the aza-imide 32 can be obtained. The aza-imide 32 can be converted to 3-aminoisonicotinic acid (11) by treatment with sodium hypobromite.

Synthesis of a specific 3-Aza acid intermediate (13) used in Scheme 4 of the present invention is shown below as Scheme 10:

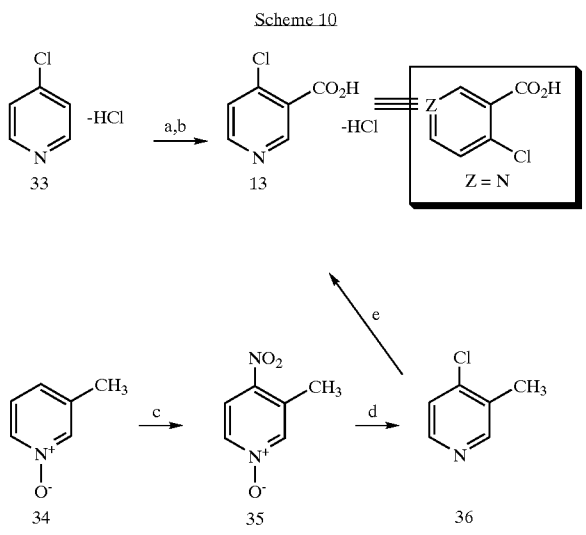

a) LDA (2 equiv); b) CO₂(g), HCl; c) HNO₃, H₂SO₄; d) PCl₃, HCl(g); e) KMnO₄

Refs: W.C.J. Ross, J. Chem. Soc. (c):1816 (1966); Taylor, Jr., et al., Org. Synth. 4:654 (1963); and Taylor, Jr., et al., J. Org. Chem. 19:1633 (1955), which are hereby incorporated by reference in their entirety.

As depicted in Scheme 10 (above), 4-chloronicotinic acid (13) can be derived from direct metallation of the commercially 4-chloropyridine (33). Alternatively, compound 13 can be derived through a sequence of steps from 3-picoline-N-oxide (34). Therefore, compound 34 can be nitrated with nitric acid and sulfuric acid to give product 35. The deoxygenation of N-oxide and displacement of the nitro group by phosphorous trichloride can lead to compound 36. Treatment of 36 with hot aqueous potassium permanganate can lead to 4-chloronicotinic acid (13).

Synthesis of the 4-Aza acid intermediate 15 used in Scheme 5 of the present invention is shown below as Scheme 11:

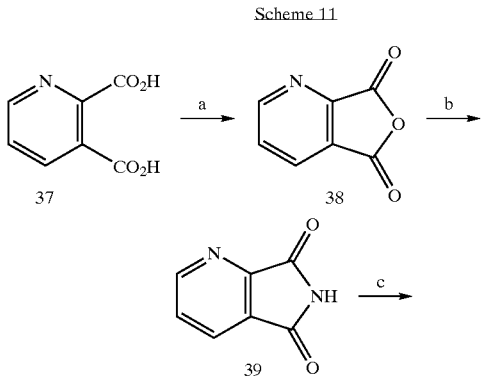

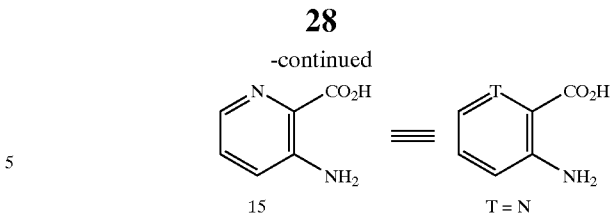

a) Acetic anhydride, reflux; b) Acetamide, reflux; c) Br₂, NaOH;

Ref: Watanabe et al., Chem. Pharm. Bull 37:36 (1989), which is hereby incorporated by reference in its entirety.

As described above in Scheme 11, compound 15 can be prepared in three steps from commercially available pyridine-2,3-dicarboxylic acid (37). Specifically, compound 37 can be converted to the oxo-imide 38 upon treatment with acetic anhydride. Upon treatment of compound 38 with acetamide, the desired aza-imide 39 can be obtained. Aza-imide 39 can be converted to the desired amino pyridine 15 upon treatment with sodium hypobromite.

An example of oxidation of the sulfur of the aza-benzothiopyranoindazoles analogues described in Scheme 1 of the present invention is shown below as Scheme 12:

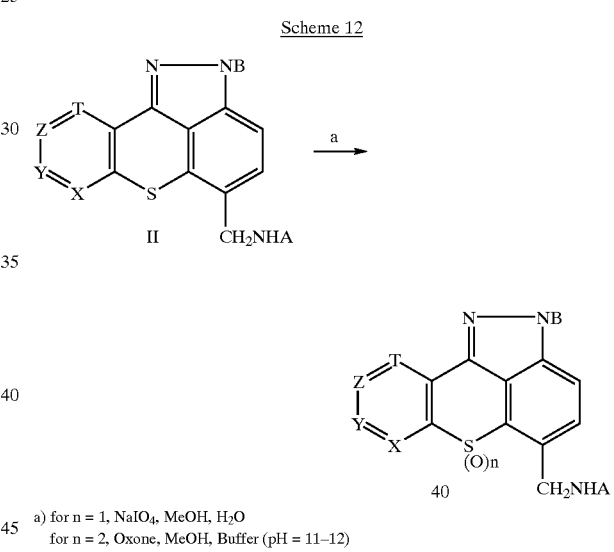

a) for n = 1, NaIO₄, MeOH, H₂O
   for n = 2, Oxone, MeOH, Buffer (pH = 11–12)

As shown in Scheme 12, compounds of formula (11), when reacted with NaIO₄, MeOH, and H₂O, can be converted to compound 40, where n is the integer 1. Moreover, compounds of formula (II) can be reacted with oxone, MeOH, and buffer (at pH 11–12) to yield compound 40, where n is the integer 2.

Another synthetic scheme for preparing compounds of formula (II) of the present invention is shown below in Scheme 13:

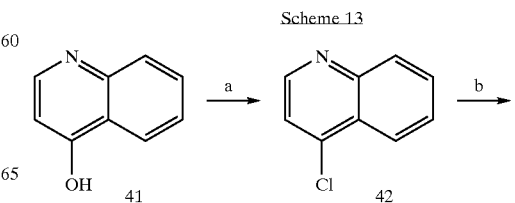

29

-continued

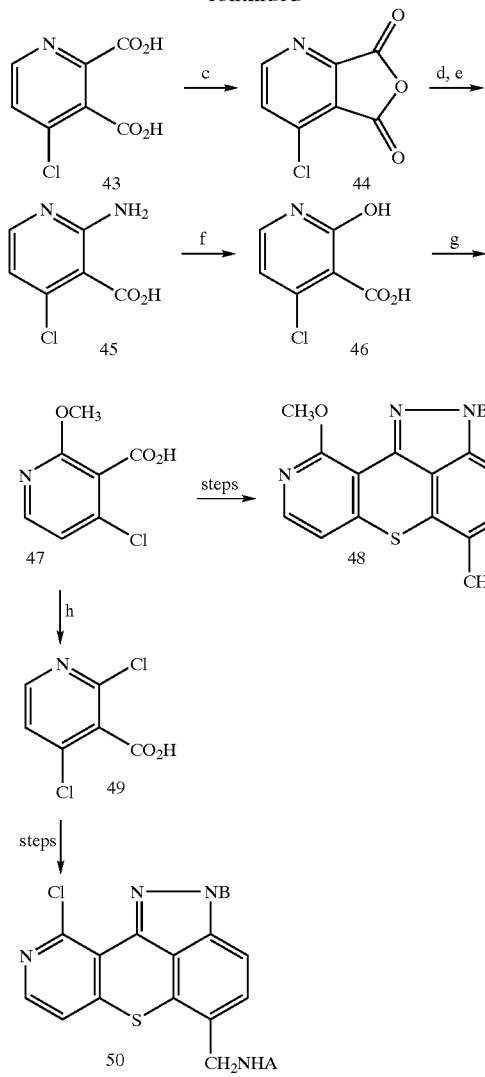

Ref: Spaeth et al., Chem. Ber. 56:2456 (1923), which is hereby incorporated by reference in its entirety.

a) POCl$_3$; b) KMnO$_4$; c) Ac$_2$O; d) Acetamide
e) Br$_2$, NaOH; f) NaNO$_2$, H$_2$SO$_4$; g) MeI, K$_2$CO$_3$
h) POCl$_3$ As depicted above in Scheme 13, 4-chloro-quinolinone (42) can be derived from quinolin-4-ol (41) using phosphorous oxychloride. Upon oxidation of compound 42 with potassium permanganate, compound 43 can be obtained. Reaction of compound 43 with acetic anhydride can yield the oxo-imide derivative 44. Compound 44 can be converted to the aza-imide upon reaction with acetamide, which is hydrolyzed to the desired amino pyridine derivative 45 upon treatment with sodium hypobromite. Diazotization of compound 45 under aqueous conditions will give the corresponding phenol derivative 46. Reaction of compound 46 with methyl iodide and potassium carbonate will yield the desired methyl ether pyridine derivative 47. Analog 47 can be further elaborated in several steps to yield compound 48 using synthetic strategies described in the present application or synthetic methodologies known by those skilled in the art. Moreover, upon reaction of analog 47 with phosphorous oxychloride, the desired 2,4-dichloro substituted pyridine derivative 49 can be obtained. Compound 49 can be converted in several steps to the desired target 50 using synthetic strategies described in the present application or using methodologies known to those skilled in the art.

Another synthetic scheme for preparing compounds of formula (II) is shown below in Scheme 14:

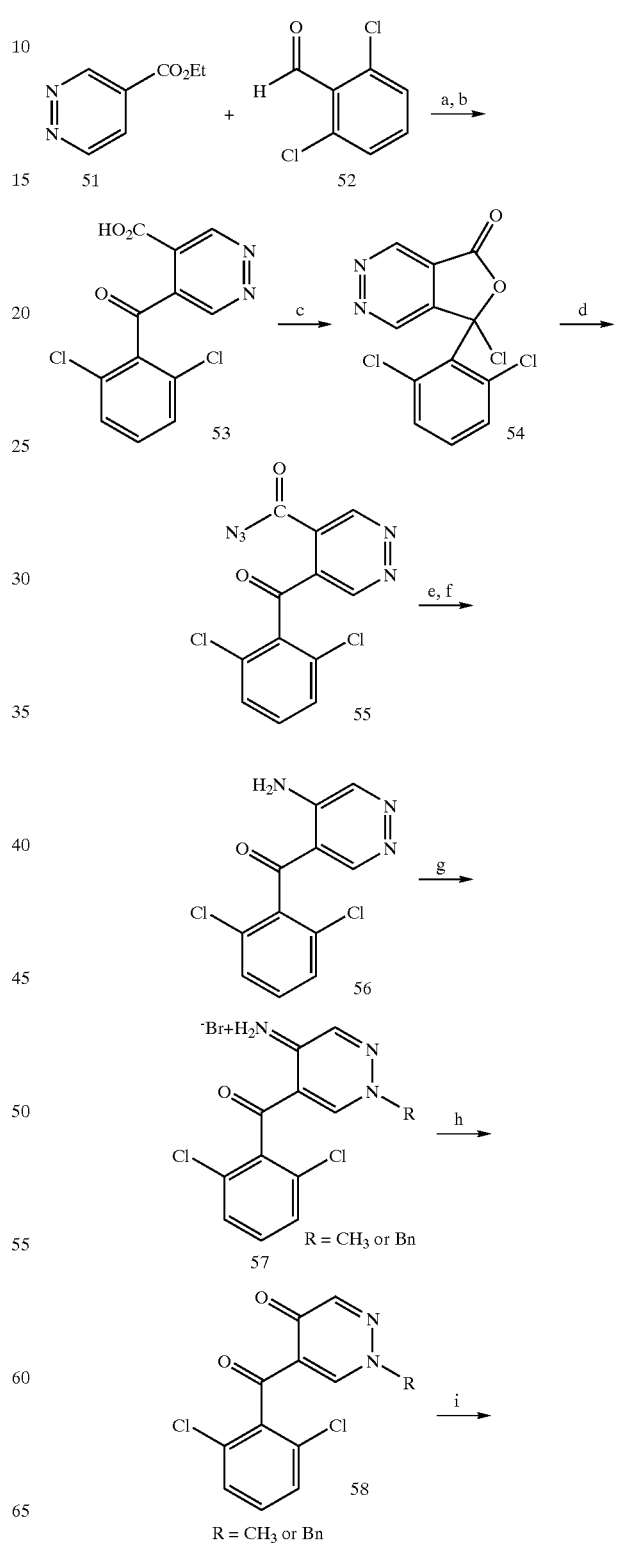

-continued

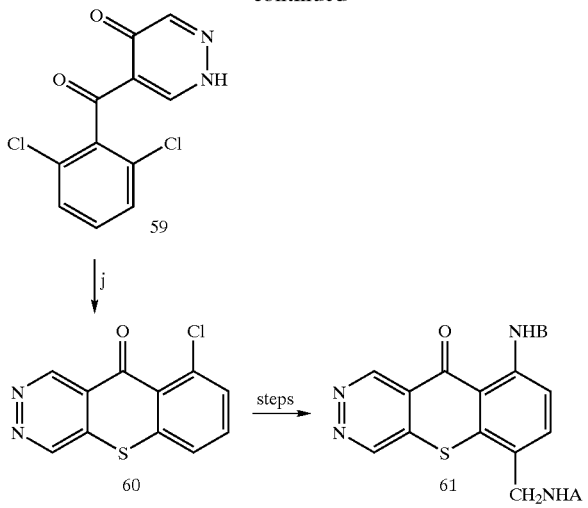

a) FeSO₄—(CH₃)₃CO₂H, HCl;  b) NaOH, EtOH; c) SOCl₂
d) NaN₃, H₂O, (CH₃)₂CO; e) Benzene; f) HCl, H₂O, Benzene
g) MeI, K₂CO₃; h) NaOH; i) AlCl₃-toluene; j) P₂S₅-pyridine Ref: Haider et al., J. Chem. Soc., Perkin Trans I (2):401–405 (1988), which is hereby incorporated by reference in its entirety.

As shown above in Scheme 14, compound 53 can be prepared by reacting pyridazine-4-carboxylic acid ethyl ester (51) with 2,6-dichlorobenzaldehyde (52) in the presence of FeSO₄—(CH₃)₃CO₂H. Ketone 53 can be converted to compound 54 upon reaction with thionyl chloride. Upon treatment of compound 54 with sodium azide, ketone 55 can be obtained. Compound 55 can be subjected to Hoffmann rearrangement conditions to give amine 56. Treatment of compound 56 with methyl iodide or benzyl iodide results in the formation of the iminium salt 57. Hydrolysis of compound 57 could lead to the formation of ketone 58. Dealkylation of 58 could afford 59. Reaction of compound 59 with phosphorous pentasulfide in refluxing pyridine yields the 2,3-diazathioxanthenone system 60. Compound 60 can be elaborated in several steps to yield the desired compound 61 using synthetic strategies described in the present application or using synthetic methodologies known to those skilled in the art.

Another preferred form of the compound of the present invention has the following formula (III):

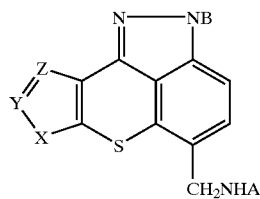

where:
X, Y, or Z=S;
A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H; C(O)OR₁; SO₂R₁; $(CH_2)_nNH(CH_2)_mCH_3$; $(CH_2)_nN((CH_2)_mCH_3)(CH_2)_pCH_3$; and $(CH_2)_nD$;
B is selected in the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; $(CH_2)_nNH(CH_2)_mCH_3$; $(CH_2)_nN((CH_2)_mCH_3)(CH_2)_pCH_3$; and $(CH_2)_nD$;

$R_1$ is selected from a group consisting of $C_1$–$C_{10}$ alkyl, phenyl, and phenyl alkyl, as free bases;

n is 2–3;

m is 0–3;

p is 0–3; and

D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom, or a pharmaceutically acceptable salt thereof.

Another preferred form of the compound of the present invention has the following formula (III):

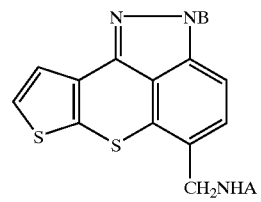

where A and B are as described above, or a pharmaceutically acceptable salt thereof.

Another preferred form of the compound of the present invention has the following formula (III):

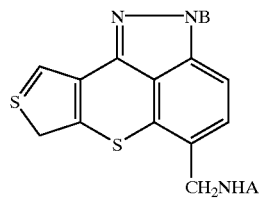

where A and B are as described above, or a pharmaceutically acceptable salt thereof.

Another preferred form of the compound of the present invention has the following formula (III):

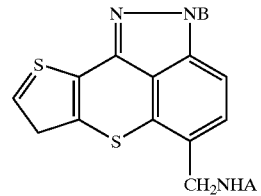

where A and B are as described above, or a pharmaceutically acceptable salt thereof.

Examples of the class of compounds according to this formula (III) are set forth in Table 3.

TABLE 3

Compounds of Formula (III)

| COMPOUND | Name of Heterocyclic System |
|---|---|
| (structure) | (2H-6,7-Dithia-1,2-diaza-cyclopenta[d]acenaphthylen-5-yl)-methylamine |
| (structure) | (2H-6,8-Dithia-1,2-diaza-cyclopenta[d]acenaphthylen-5-yl)-methylamine |
| (structure) | (2H-6,9-Dithia-1,2-diaza-cyclopenta[d]acenaphthylen-5-yl)-methylamine |

Synthesis of the thiophene derivatives of formula (III) of the present invention is shown below as Scheme 15.

Scheme 15

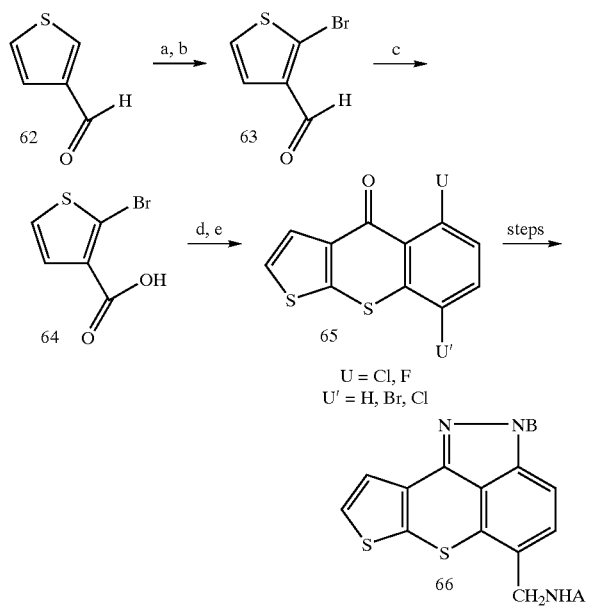

a) HO(CH$_2$)$_2$OH, p-TSOH; b) n-BuLi, Br$_2$; c) AgO;
d) 3-chloro-thiophenol, K$_2$CO$_3$, DMF; e) H$_2$SO$_4$ Ref: Archer et al., J. Chem. Soc. Perkin Trans. 2 813–820 (1983), which is hereby incorporated by reference in its entirety.

As described in Scheme 15, compound 63 can be prepared from bromination reaction of commercially available thiophene-3-carbaldehyde (62) which is first protected as diacetal. Compound 63 can be further oxidized to the carboxylic acid derivative 64 using silver oxide. Coupling of 64 with the appropriate 2,5-disubstituted thiophenol followed by cyclization yields the tricyclic system 65. Compound 65 can be further elaborated to yield compound 66 using synthetic steps described in the present application or using synthetic methodologies known to those skilled in the art.

The present invention is also directed to a method for inhibiting cell proliferation in mammals. This method involves administering to a mammal a therapeutically effective amount of the compound of the following formula, and as described above:

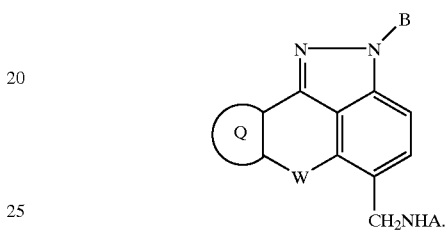

The present invention is also directed to a pharmaceutical composition of matter including the following compound and one or more pharmaceutical excipients:

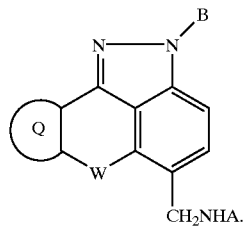

Based on the results obtained in the standard pharmacological test procedures described below, the compounds of the present invention are useful as antineoplastic agents. More particularly, the compounds of the present invention are useful for inhibiting the growth of neoplastic cells, causing cell death of neoplastic cells, and eradicating neoplastic cells. The compounds of the present invention are, therefore, useful for treating solid tumors, including sarcomas and carcinomas, such as astrocytomas, prostate cancer, breast cancer, small cell lung cancer, and ovarian cancer, leukemias, lymphomas, adult T-cell leukemia/lymphoma, and other neoplastic disease states.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycolor polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

EXAMPLES

The numbers used to identify the compounds described in the following examples do not necessarily correspond to those numbers used to identify compounds in the preceding schemes.

In Examples 1–2, compounds were synthesized according to Scheme 16 as follows:

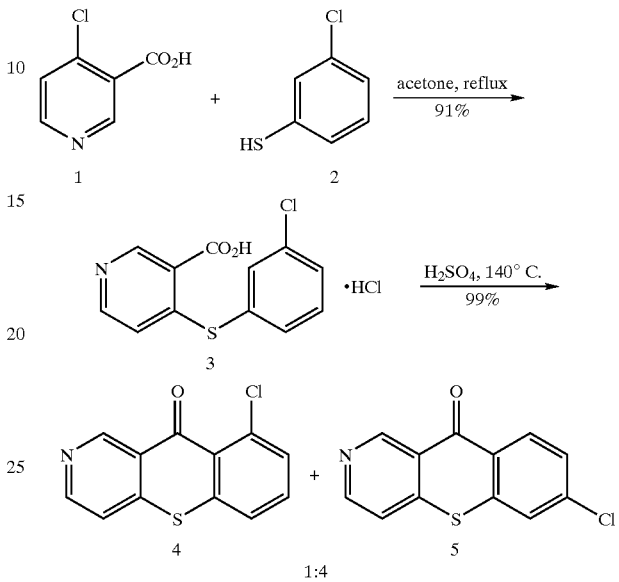

Example-1

Preparation of Compound 3 of Scheme 16

A solution of 3-chlorothiophenol (2, 5.35 g, 0.106 moles) in anhydrous acetone (50 mL), was added to a mixture of chloronicotinic acid (1, 12.55 g, 0.079 mol) in anhydrous acetone under nitrogen. The milky white suspension was refluxed for three hours. Upon cooling to room temperature, the precipitate was collected by filtration. The residue was then washed with cold acetone to afford a white solid. This solid was air dried and placed in an oven at 40° C. (19.5 g, 91% yield): $^1$H NMR (300 MHz, DMSO) δ 9.08 (s, 1H), 8.54 (d, 1H, J=6.26 Hz), 7.79–7.66 (m, 4H), 6.97–6.95 (d, J=6.25 Hz, 1H) ppm.

Example-2

Preparation of Compounds 4 and 5 of Scheme 16

Sulphuric acid (20 mL) was placed in a round bottom flask under an atmosphere of nitrogen and the flask was placed in an oil bath which was pre-heated to 100° C. Compound 3 (5.0 g, 0.061 moles) was added over 30 minutes to the sulphuric acid in small increments and left to dissolve before adding more whilst stirring. The dark red solution was heated at 130° C. for three hours. The solution was then cooled in an ice bath and crushed ice was added to give a thick white suspension. The solid (4.08 g, 99%) was collected by filtration and dried in an oven to give a mixture of two regioisomers 4 and 5, inseparable by column chromatography.

In Examples 3–8, compounds were synthesized according to Scheme 17 as follows:

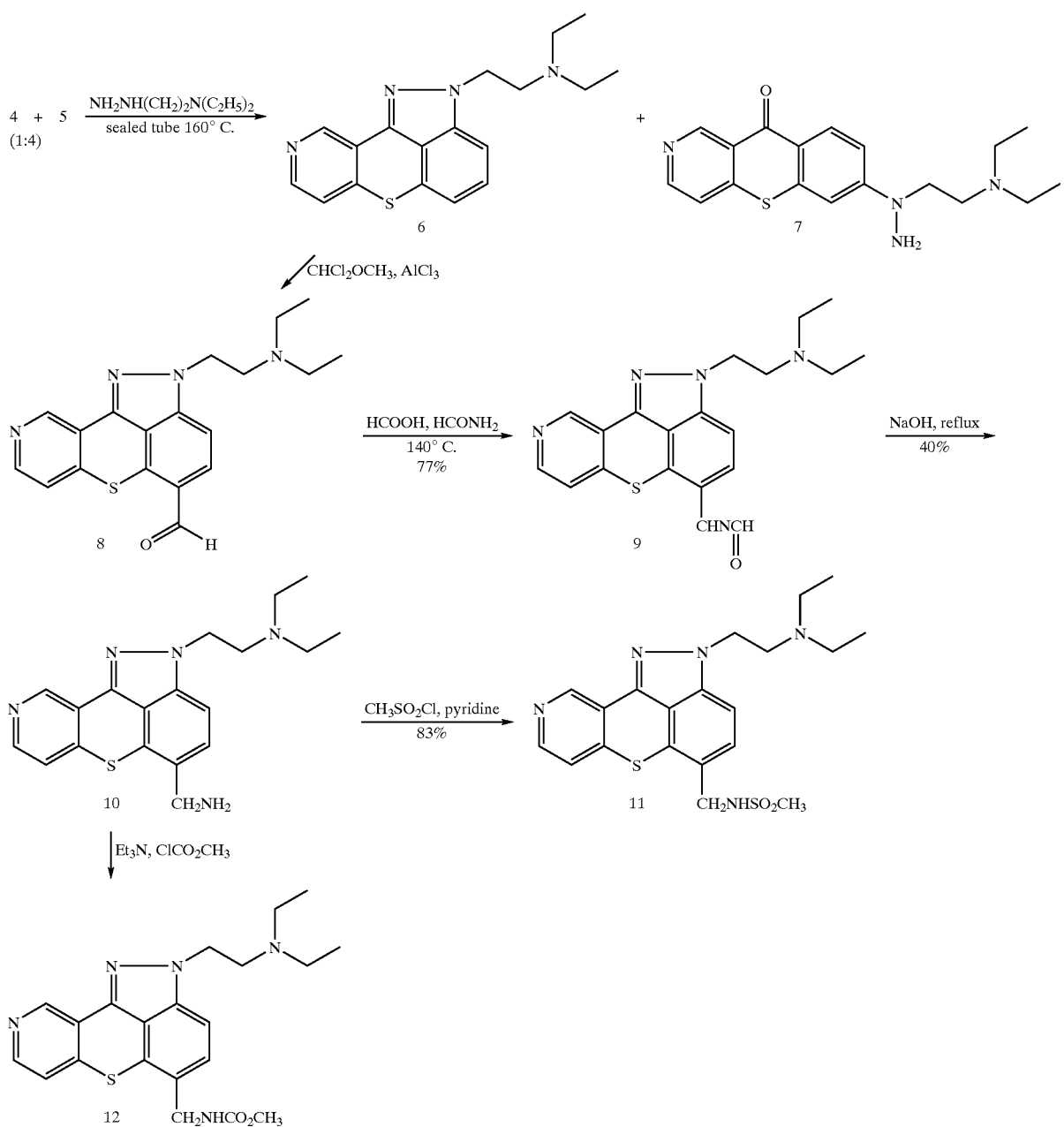

Scheme 17

Example-3

Preparation of Compounds 6 and 7 of Scheme 17

A mixture of compound 4 and its isomer compound 5 (1:4, 5 g, 0.020 moles) along with N-2-(dimethylaminoethyl)hydrazine (7.95 g, 0.061 moles) was placed in a sealed tube and heated to 140° C. whilst stirring for 5 hours. Upon cooling to room temperature, water was added and the solution was basified with NaOH (35%). The aqueous mixture was extracted using dichloromethane (300 mL) and the organic filtrates were reduced to an oily residue, which was purified by column chromatography (30 cm×8 cm). The desired product 6 (1.26 g, 97%) was isolated along with the regioisomer 7 (1.03 g, 20%). Compound 6: $^1$H NMR (300 MHz, CDCl$_3$) δ 9.16 (s, 1H), 8.29 (d, J=5.46 Hz, 1H), 7.19 (d, J=8.10 Hz, 1H), 7.13 (d, J=5.51, 1H), 6.97 (d, J=8.44 Hz, 1H), 6.71 (d, J=7.17 Hz, 1H), 4.35 (t, J=6.75 Hz, 2H), 2.95 (t, J—7.14 Hz, 2H), 2.58 (q, J=7.12 Hz, 4H), 1.03 (t, J=6.01 Hz, 6H) ppm. Compound 7: $^1$H NMR (300 MHz, CDCl$_3$) δ 9.62 (s, 1H), 8.57 (t, J=3.23 Hz, 1H), 8.41 (t, J=7.43 Hz, 1H), 7.36 (d, J=5.09 Hz, 1H), 7.01 (d, J=2.5 Hz, 1H), 6.73–6.72 (d, J =2.30 Hz, 1H), 4.47 (s, 2H), 3.68 (t, 2H, J=5.59 Hz), 2.75 (t, J=5.77 Hz, 2H), 2.53 (q, J=7.13 Hz, 4H), 0.98 (t, J=7.10 Hz, 6H) ppm.

Example-4

Preparation of Compound 8 of Scheme 17

A suspension of aluminum chloride (2.76 g, 0.021 moles) in dichloroethane (50 mL) was stirred at room temperature for 15 minutes under nitrogen, and a solution of compound 6 (1.68 g, 0.0052 moles) in dichloroethane (40 mL) was added at 5° C. The resulting mixture was stirred for 10 minutes and cooled to 0° C. Triethylamine (1.05 g, 0.0104 moles) was then added to the mixture. A solution of dichloromethyl methyl ether (2.38 g, 0.021 moles) in dichloroethane was added dropwise over a period of 15 minutes. The mixture was refluxed for 3 hours, and diluted with 2 N hydrochloric acid (20 mL). The mixture was then poured over chloroform (250 ML) and basified with 6 N sodium hydroxide (pH 8–9) and the layers were separated. The aqueous layer was extracted with chloroform (100 mL). The combined organic layers were washed with water, dried over sodium sulfate, and concentrated in vacuum to give a crude 8 (1.55 g, 85%). This material was used in subsequent reaction without further purification.

Example-5

Preparation of Compound 9 of Scheme 17

A mixture of compound 8 (0.72 g, 0.00203 moles) in formamide (14 mL) and formic acid (1 mL), was refluxed at 145° C. for 4 hours under nitrogen. The mixture was then allowed to cool to room temperature and crushed ice was added to the flask. Upon basification with NaOH (35%, ~2 mL), the aqueous mixture was extracted with ethyl acetate (3×20 mL) and the organic layers were dried over sodium sulfate. The organic layer was reduced to dryness to give the desired product, which was purified by column chromatography to give 9 as a red/orange powder (0.68 mg, 77%): $^1$H NMR (300 MHz, CDCl$_3$) δ 9.16 (s, 1H), 8.30–8.25 (m, 2H), 7.22–7.19 (d, J=8.6 Hz, 1H), 7.17–7.15 (d, J=5.56 Hz, 1H), 6.98–6.96 (d, J=8.55 Hz, 1H), 5.50–5.90 (m, 1H), 4.44–4.42 (d, J=5.70 Hz, 2H), 4.38–4.33 (t, J=6.92 Hz, 2H), 2.96–2.91 (t, J=6.97 Hz, 2H), 2.61–2.54 (q, J=7.15 Hz, 4H), 1.01–0.96 (t, J=7.11 Hz, 6H) ppm.

Example-6

Preparation of Compound 10 of Scheme 17

To a solution of Compound 9 (0.88 g, 0.00023 moles) and methanol (4 mL), NaOH (10%, 2 mL) was added to the flask and stirred whilst under N$_2$ and the mixture was refluxed for four hours. The reaction mixture was cooled to room temperature and extracted with chloroform. The organic layers were washed with water, dried over sodium sulfate and concentrated in vacuum to an oily residue which was purified by column chromatography to give the desired product 10 (32 mg, 40%): $^1$H NMR (300 MHz, CDCl$_3$) δ 9.17 (s, 1H), 8.31–8.29 (d, 1H, J=5.45 Hz), 7.24–7.19 (d, J=14.4 Hz, 1H), 7.19–7.18 (d, J=5.05 Hz, 1H), 7.04–7.01 (d, J=8.50 Hz, 1H), 4.47–4.42 (t, J=6.86 Hz, 2H), 3.12–3.00 (t, J=6.8 Hz, 2H), 2.68–2.61 (q, J=7.14 Hz, 4H), 1.48–1.39 (t, J=7.31 Hz, 6H) ppm.

Example-7

Preparation of Compound 11 of Scheme 17

To a mixture of compound 10 (0.192 g, 0.00054 moles) in anhydrous methylene chloride (15 mL), was added anhydrous pyridine (0.2 mL) at 0° C. under N$_2$. Methanesulfonyl chloride (0.072 g, 0.00063 moles) was added to the flask and the reaction mixture was stirred at 0° C. for half an hour and then allowed to warm to room temperature over 1.5 hours. Water (6 ml) was then added to the flask, followed by NaOH (35%, 2 drops) to basify the solution. The aqueous mixture was extracted with dichloromethane (10 mL) and the resulting organic layers were dried over sodium sulfate. The filtrate was reduced to dryness under vacuum and the oily residue was purified by column chromatography (2:1, dichloromethane/DMA, 30 cm×3 cm) to give the desired product 11 as yellow solid (193 mg, 83%): $^1$H NMR (300 MHz, CDCl$_3$) δ 9.20 (s, 1H), 8.33 (d, J=5.5 Hz, 1H), 7.27 (m, 1H), 7.19 (d, J=8.6 Hz, 1H), 7.01 (d, J=8.6 Hz, 1H), 4.38 (t,J =6.8 Hz, 2H), 4.29 (d, J=5.6 Hz, 2H), 2.95 (t, J=7.0 Hz, 2H), 2.91 (s, 3H), 2.58 (q, J=7.1 Hz, 4H), 0.98 (t, J=7.1 Hz, 6H) ppm.

Example-8

Preparation of Compound 12 of Scheme 17

To a solution of the free base of 10 (0.046 g, 0.00013 moles) in dichloromethane (3.0 mL) were added methyl chloroformate (0.015 mL) and triethylamine (0.05 mL) with stirring at 0° C. The mixture was stirred for two hours and allowed to warm to room temperature. The reaction mixture was partitioned between dichloromethane and water. The organic phase was extracted, dried over sodium sulfate, and concentrated in vacuum to give an oily residue which was purified by column chromatography to give the desired product 12 (28 mg, 53%): $^1$H NMR (300 MHz, CDCl$_3$) δ 9.18 (s, 1H), 8.32–8.30 (d, J=5.45 Hz, 1H), 7.19–7.17 (d, J=5.5 Hz, 1H), 6.99–6.96 (d, J=8.5 Hz, 1H), 4.99 (m, 1H), 4.39–4.30 (m, 4H), 3.71 (s, 3H), 2.97–2.55 (m, 2H), 2.62–2.55 (m, 4H), 1.6–0.83 (m, 6H) ppm.

In Examples 9–13, compounds were synthesized according to Scheme 18 as follows:

Scheme 18

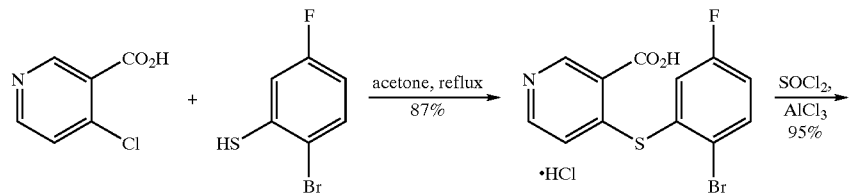

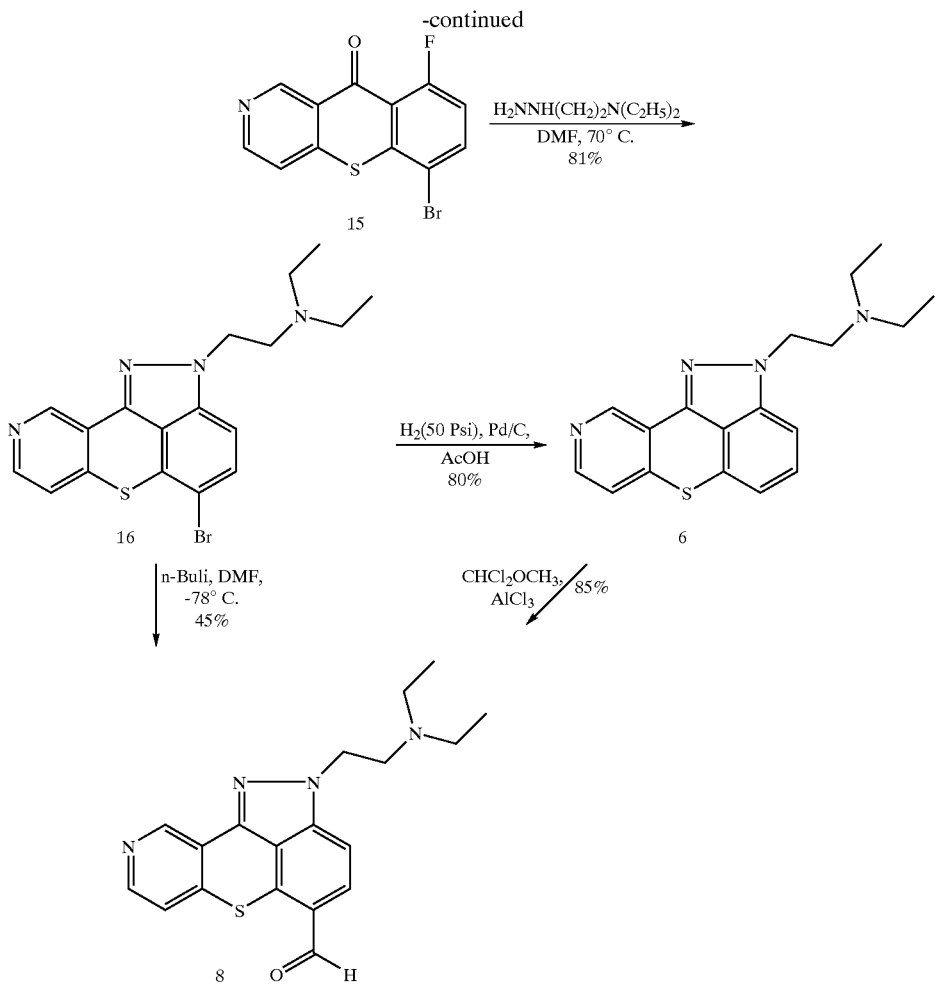

Example-9

Preparation of Compound 14 of Scheme 18

A solution of compound 13 (0.657 g, 3.17 mmol) in anhydrous acetone (5 mL) was added to a mixture of 4-chloronicotinic acid (1, 0.50 g, 3.17 mmol) in anhydrous acetone under nitrogen. The milky white suspension was refluxed for three hours. Upon cooling to room temperature, the precipitate was collected by filtration. The residue was then washed with cold acetone to afford compound 14 as a white solid. This solid was dried in an oven at 40° C. (1.01 g, 87% yield): $^1$H NMR (300 MHz, DMSO) δ 9.05 (s, 1H), 8.47–8.45 (d, J=5.80 Hz, 1H), 8.01–7.96 (m, 1H), 7.83–7.79 (m, 1H), 7.51–7.44 (m, 1H), 6.65–6.63 (d, J=5.76 Hz, 1H) ppm.

Example-10

Preparation of Compound 15 of Scheme 18

A mixture of acid 14 (0.50 g, 1.53 mmol) and thionyl chloride (3.0 mL) was refluxed for 15 hours until a pale yellow solution is obtained. The excess thionyl chloride was removed by vacuum aspiration. The residue was then dissolved in nitrobenzene (5.0 mL), followed with the addition of aluminium chloride (1.02 g, 7.65 mmol) portionwise over the course of 30 minutes at room temperature. This dark-red solution was heated in an oil bath at 100° C. for 5 hours and poured on ice. The excess nitrobenzene was removed by steam distillation and the precipitate obtained was filtered and washed with ligroin. The residue was collected and dried in a vacuum oven to give the desired compound 15 (227 mg, 65%) (based on the unreacted starting material): $^1$H NMR (300 MHz, DMSO) δ 9.34 (s, 1H), 8.77 (d, J=5.52 Hz, 1H), 8.21 (m, 1H), 8.09–7.94 (m, 1H), 7.48–7.39 (m, 1H) ppm.

Example-11

Preparation of Compound 16 of Scheme 18

A mixture of compound 15 (125 mg, 0.41 mmol) in anhydrous DMF (0.5 mL) was treated with N-2-(diethylaminoethyl)hydrazine (106 mg, 0.81 mmol) and the mixture was heated at 70° C. for 2 hours. Upon cooling to room temperature, water was added. The aqueous mixture was extracted using dichloromethane (2×3 mL) and the organic filtrates were reduced to an oily residue, which was purified by column chromatography eluting with 1:3, CMA (18% chloroform, 80% methanol, 2% ammonium hydroxide)/methylene chloride. The desired product 16 (126 mg, 81%) was isolated as an orange solid: $^1$H NMR (300 MHz, CDCl$_3$) δ 9.19 (s, 1H), 8.35 (d, J=4.20 Hz, 1H), 7.32 (m, 1H), 7.22 (d, J=4.20, 1H), 6.94 (m, 1H), 4.38 (t, J=6.90 Hz, 2H), 2.96 (t, J=6.97 Hz, 2H), 2.59 (q, J=6.00 Hz, 4H), 0.98 (t, J=6.00 Hz, 6H) ppm.

Example-12

Preparation of Compound 6 of Scheme 18

A mixture of compound 16 (11 mg) in AcOH/EtOH (1:9) (1.5 mL) was reduced using 5% Pd/C under $H_{2(g)}$ (50 Psi) for four hours. The mixture was filtered over a celite bed and the filtrate was basified with 6 N NaOH. The aqueous mixture was extracted with methylene chloride (3×5 mL). The organic extracts were dried over sodium sulfate and concentrated to dryness to give the desired product 6 (7.0 mg, 80%): $^1$H NMR (300 MHz, CDCl$_3$) δ 9.16 (s, 1H), 8.29–8.28 (d, J=5.46 Hz, 1H), 7.20–7.18 (d, J=8.10 Hz, 1H), 7.14–7.12 (d, J=5.51, 1H), 6.99–6.96 (d, J=8.44 Hz, 1H), 6.73–6.70 (d, J=7.17 Hz, 1H), 4.39–4.34 (t, J=6.75 Hz, 2H), 2.97–2.92 (t, J=7.14 Hz, 2H), 2.62–2.55 (q, J=7.12 Hz, 4H), 1.05–1.00 (t, J=6.01 Hz, 6H) ppm.

Example-13

Preparation of Compound 8 of Scheme 18

A solution of compound 16 (1.0 g, 2.48 mmoles) in anhydrous Tetrahydrofuran (THF) (20 mL) was cooled to −78° C. DMF (272 mg, 0.3 mL, 1.5 equivalents) was added at −78° C., and the mixture was allowed to stir at −78° C. Followed, n-BuLi (2.48 mL, 2.5 equivalents, 2.5 M in hexanes) were added and the mixture was vigorously stirred at −78° C. for 1 hour and additional 45 minutes at −45° C. The reaction was quenched with 3 N HCl (0.5 mL) and extracted with methylene chloride (3×30 mL). The organic layers were concentrated to dryness and the residue was purified by flash column chromatography to give the title compound 8.

Compound 13 of Scheme 18 can be synthesized as illustrated below in Scheme 19.

Scheme 19

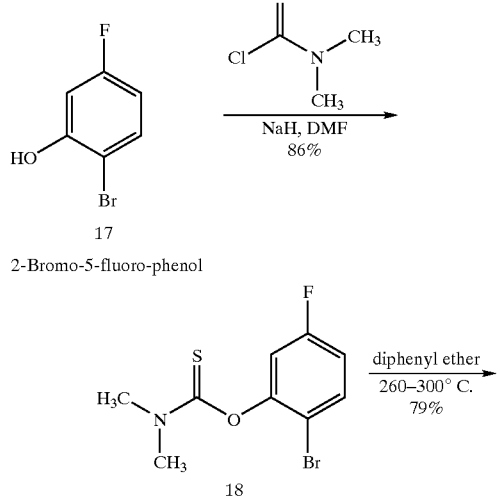

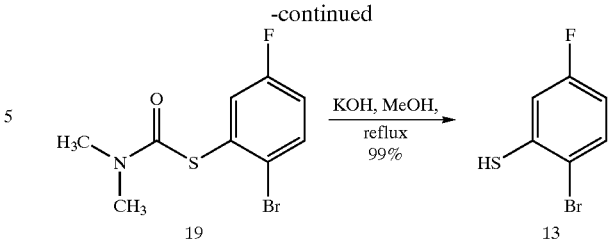

Example 14

Preparation of Compound 18 of Scheme 19

A solution of 2-bromo-5-fluro-phenol (4.63 g, 24.1 mmol) in anhydrous DMF (50 mL), cooled to 0° C. in an ice bath for 15 minutes, was treated NaH (60% wt/wt) (1.45 g, 1.50 equivalents. This mixture was stirred at 0° C. for 15 minutes followed with the addition of N,N-dimethylthiocarbamoyl chloride (4.5 g, 36.4 mmol). Upon stirring for 15 hours, the reaction mixture was quenched over ice-water (200 mL) and extracted with diethyl ether (3×100 mL). The organic layers were separated, dried over Na$_2$SO$_4$ and concentrated to dryness. The residue obtained was purified by column chromatography eluting with 90% Hexanes, Ethyl acetate to give the desired product as nice white solid (5.8 g, 86%): $^1$H NMR (300 MHz, CDCl$_3$) δ 7.62–7.52 (m, 1H), 6.99–6.87 (m 2H), 3.45 (s, 3H), 3.40 (s, 3H) ppm.

Example 15

Experimentals for Compound 19 of Scheme 19

A mixture of compound 19 (5.5 g) in diphenyl ether (30 mL) was heated in a sand bath at temperature 260–300° C. After 5 hours of heating, the TLC (80:20, Hexanes, Ethyl acetate) showed 90% conversion. The reaction was cooled to room temperature and purified by column chromatography eluting with 90% Hexanes, Ethyl acetate to give the desired product 20 as a nice white solid (4.32 g, 79%): $^1$H NMR (300 MHz, CDCl$_3$) δ 7.65–7.60 (q, J=5.36, 3.02 Hz, 1H), 7.41–7.38 (q, J=3.02 Hz, 1H,), 7.02–7.95 (m, 1H), 3.0–3.2 (m, 6H) ppm

Example 16

Experimentals for Compound 13 of Scheme 19

A mixture of compound 20 (4.3 g, 15.5 mmol) and powdered KOH (4.3 g, 89.7 mmol) in methanol (300 mL) was heated to reflux for 3 hours. The solvent was removed under vacuum, and the residue was portioned between water (50 mL) and methylene chloride (50 mL). The aqueous layer was separated, acidified to pH 3 with 6 N HCl and reextracted with methylene chloride (3×100 mL). The organic layers were dried over Na$_2$SO$_4$ and concentrated to dryness to give the desired product 13 as pale yellow oil (3.3 g, 99%): $^1$H NMR (300 MHz, CDCl$_3$) δ 7.50–7.45 (m 1H), 7.18–7.10 (m, 1H), 6.75–6.71 (m, 1H), 4.08 (s, 1H) ppm.

In Examples 17–20, compounds were synthesized according to Scheme 20 as follows:

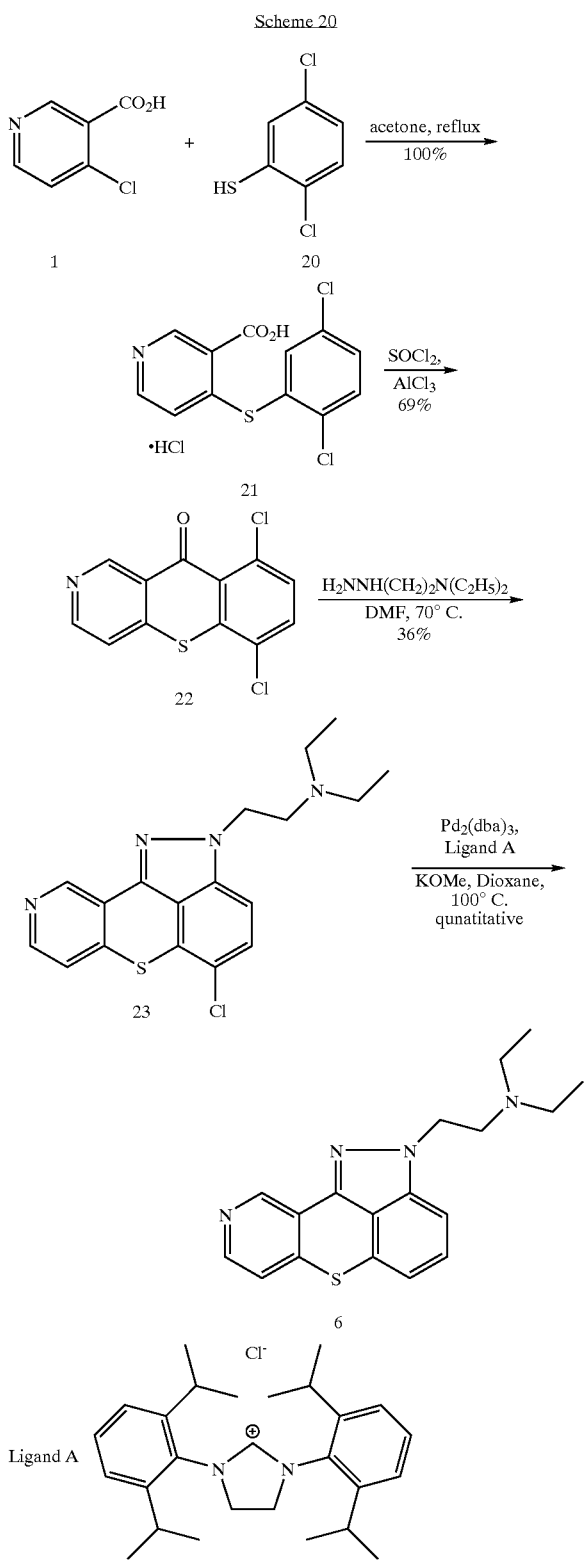

Example 17

Experimentals for Compound 21 of Scheme 20

A solution of 2,5-dichlorothiophenol (5.2 g) in dry acetone (25 mL) was added to a solution of 4-chloronicotinic acid (1, 4.5 g) in dry acetone (50 mL). The mixture was then refluxed for 3 hours and then allowed to cool to room temperature. The suspension was then filtered and washed with acetone and the residue was dried under vacuum to give the desired product 21 (8.6 g, 100%) as a white solid: $^1$H NMR (300 MHz, CDCl$_3$) δ 9.17 (s, 1H), 8.61–8.60 (d, J=6.1 Hz, 1H), 8.07–8.06 (m, 1H), 7.93–7.90 (d, J=8.6 Hz, 1H), 7.86–7.83 (m, 1H), 6.97–6.95 (d, J=6.1 Hz, 1H) ppm.

Example 18

Experimentals for Compound 22 of Scheme 20

A mixture of the acid 21 (8.0 g) and thionyl chloride (80 mL) was refluxed for 15 hours until a pale yellow solution is obtained. The excess of thionyl chloride was removed by vacuum aspiration. The residue was then dissolved in nitrobenzene (100 mL), followed with aluminium chloride (17 g, 127 mmol). This dark-red solution was heated in an oil bath at 125° C. for 4 hours and poured onto ice and sonicated. The resulting solids were collected by filtration and washed thoroughly with ligroine and heptane to remove the excess nitrobenzene. The residue was collected and dried in a vacuum oven to give the desired product 22 (5.2 g, 69%): $^1$H NMR (300 MHz, CDCl$_3$) δ 9.45 (s, 1H), 8.65–8.64 (d, J=5.6 Hz, 1H), 7.58–7.56 (d, J=8.3 Hz, 1H), 7.49–7.46 (m, 1H), 7.21 (s, 1H) ppm.

Example 19

Experimentals for Compound 23 of Scheme 20

A mixture of compound 22 (3.75 g) in anhydrous DMF (50 mL) was treated with N-2-(diethylaminoethyl)hydrazine (4 g) and the mixture was heated at 70° C. for 4 hours. Upon cooling to room temperature, water was added. The aqueous mixture was extracted using dichloromethane (2×3 mL) and the organic filtrates were reduced to an oily residue, which was purified by column chromatography (60:40 Ethyl acetate/Methanol). The desired product was further purified by crystallization from ethyl acetate and heptane to give the desired product 23 (1.7 g, 35.6%): $^1$H NMR (300 MHz, CDCl$_3$) δ 9.09 (s, 1H), 8.27–8.25 (m, 1H), 7.20–7.10 (m, 2H), 6.96–6.93 (m, 1H), 4.38 (m, 2H), 2.95 (m, 2H), 2.58–2.55 (m, 4H), 0.98–0.94 (t, J=7.1 Hz, 6H) ppm.

Example 20

Experimentals for Compound 6 of Scheme 20

To a mixture of compound 23 (100 mg) in dioxane (2.5 mL), Pd$_2$(db)$_3$ (5 mg, 2 mol %) and ligand A (2 mol %) were added under argon. Potassium methoxide (2 equivalents) was then added and the reaction mixture was heated at 100° C. for 2½ hours. After cooling to room temperature the reaction mixture was diluted with ethyl acetate and filtered through a celite bed. The filtrate was concentrated down under reduced pressure to yield the desired product 6 (89 mg) in quantitative yield.

In Examples 21–24, compounds were synthesized according to Scheme 21.

Scheme 21

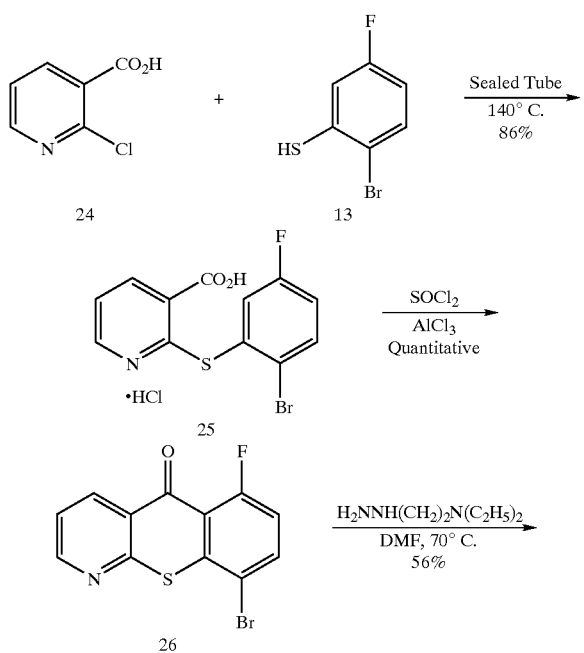

Example 21

Experimentals for Compound 25 of Scheme 21

A mixture of 2-chloronicotinic acid (24, 3.04 g, 19.3 mmol) and 2-bromo-5-fluoro-thiophenol (13, 6.0 g, 28.9 mmol) was heated at 140° C. in a sealed tube for 6 hours. The mixture was then allowed to cool to room temperature and the residue was filtered, rinsed with cold acetone to yield the desired product 25 (5.75 g, 86%) as a white solid: $^1$H NMR (300 MHz, DMSO) δ 8.46 (q, J=1.8 Hz, 1H), 8.27 (q, J=1.8 Hz, 1H), 7.80 (q, J=5.5 Hz, 1H), 7.61 (q, J=3.1 Hz, 1H), 7.32–7.26 (m, 2H) ppm.

Example 22

Experimentals for Compound 26 of Scheme 21

A mixture of compound 25 (5.75 g, 17.6 mmol) and thionyl chloride (25 mL) was refluxed under $N_2$ at 95° C. for 2 hours. The clear solution was then allowed to cool to room temperature, and the excess thionyl chloride was removed from the residue via vacuum aspiration to yield a yellow solid. The latter residue was dissolved in nitrobenzene (25 mL) and aluminium chloride (11.73 g, 0.088 mol) was added portionwise over half an hour. The mixture was then heated at 100° C. for 5½ hours then allowed to cool to room temperature, poured over 400 mL of crushed ice and sonicated. The resulting solid was filtered and washed thoroughly with heptane and ligroine. The remaining residue was placed on the pump at 50° C. to remove excess nitrobenzene. The desired compound 26 (5.43 g, 100%) was obtained as a grey solid: $^1$H NMR (300 MHz, CDCl$_3$) δ 8.82 (q, J=1.9 Hz, 1H), 8.72 (q, J=1.9 Hz, 1H), 7.86 (q, J=4.6 Hz, 1H), 7.52 (m, 1H), 7.10 (m, 1H) ppm.

Example 23

Experimentals for Compound 27 of Scheme 21

A mixture of compound 26 (5.43 g, 17.6 mmol) and N-2-diethylaminoethylhydrazine (3.46 g, 26.3 mmol) in DMF was heated at 70° C. for 16 hours. The residue was then allowed to cool to room temperature, water was added and the compound was extracted with dichloromethane. The organic layers were then dried over sodium sulfate and concentrated down. The resulting residue was then purified by column chromatography (3:1 dichloromethane/CMA) to yield compound 27 as yellow/orange crystals (3.97 g, 56%): $^1$H NMR (300 MHz, CDCl$_3$) δ 8.37 (q, J=1.8 Hz, 1H), 8.23 (m, 1H), 7.30 (t, J=2.6 Hz, 1H), 7.17 (m, 1H), 6.89 (d, J=8.8 Hz, 1H), 4.33 (m, 2H), 2.89 (m, 2H), 2.55 (m, 4H), 0.97 (t, J=7.1 Hz, 6H) ppm.

Example 24

Experimentals for Compound 28 of Scheme 21

Compound 27 (1.0 g, 2.48 mmol) in THF (5 mL) under $N_2$ was then cooled to −78° C. in a dry ice/acetone bath. DMF (63 mg, 0.87 mmol) was then added dropwise and the mixture was allowed to stir for fifteen minutes. Butylithium (1.7 mmol) was then added dropwise and stirred for 1½ hours at −78° C. The residue was allowed to warm to 0° C. followed by the addition of a few drops of HCl (3 N). The solution was basified with NaOH (6 N) and extracted with dichloromethane. The organic layers where combined and dried over sodium sulfate, then concentrated down and the residue purified using column chromatography (dichloromethane/CMA, 3:1). The desired product 28 was obtained as a yellow/orange solid (696 mg, 79%/.). $^1$H NMR (300 MHz, CDCl$_3$), δ 10.08 (s, 1H), 8.52 (m, 1H), 8.39 (m, 1H), 7.70 (m, 1H), 7.30 (m, 1H), 7.08 (d, J=8.7 Hz, 1H), 4.42 (m, 2H), 3.00–2.89 (m, 2H), 2.56 (q, J=7.0 Hz, 4H), 0.98 (m, 6H) ppm.

In Examples 25–28, compounds were synthesized according to Scheme 22 as follows:

Scheme 22

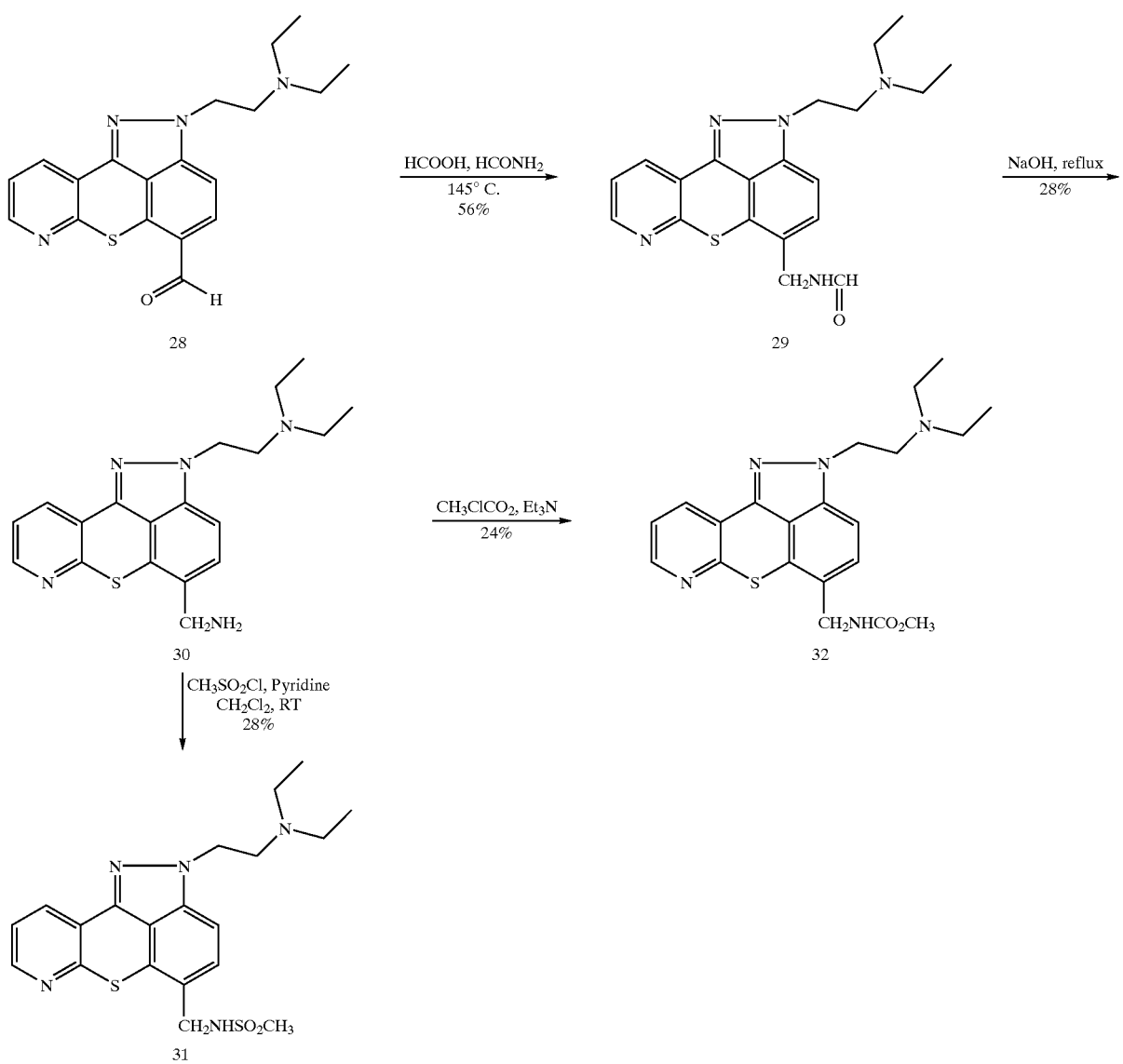

Example 25

Experimentals for Compound 29 of Scheme 22

A mixture of compound 28 (165 mg, 0.46 mmol) and formic acid (170 mg, 3.7 mmol) under $N_2$ in formamide (10 mL) was stirred at 145° C. for 3 hours. The reaction mixture was allowed to cool to room temperature, and further cooled in an ice bath and crushed ice was added. The reaction mixture was basified with NaOH (6N) and extracted with dichloromethane. The organic layers were dried over sodium sulfate and concentrated down. The resulting residue was purified by column chromatography (3:1 dichloromethane/CMA) to yield the desired compound 29 (98 mg, 56%): $^1$H NMR (300 MHz, CDCl$_3$) δ 8.37 (m, 1H), 8.34–8.16 (m, 2H), 7.20–7.11 (m, 1H), 7.02 (d, J=8.1 Hz, 1H), 4.46 (d, J=5.7 Hz, 2H), 4.35 (m, 2H), 2.93 (m, 2H), 2.60–2.53 (m, 4H), 1.26 (m, 6H) ppm.

Example 26

Experimentals for Compound 30 of Scheme 22

A mixture of Compound 29 (778 mg, 2.0 mmol) and NaOH (10%, 15 mL) in methanol (30 mL) under $N_2$ was heated at 90° C. for 1¼ hours. The residue was concentrated down and then extracted with dichloromethane. The organic layers were then dried over sodium sulfate and concentrated to form the desired product 30 (195 mg, 28%): $^1$H NMR (300 MHz, CDCl$_3$) δ 8.33 (q, J=3.0 Hz, 1H), 8.24 (q, J=6.0 Hz, 1H), 7.26 (m, 1H), 7.14 (m, 1H), 6.96 (d, J=8.5 Hz, 1H), 4.5 (t, J=7.0 Hz, 2H), 3.84 (s, 2H), 2.94 (t, J=7.2 Hz, 2H), 2.58 (q, J=7.1 Hz, 4H), 1.00 (m, 6H) ppm.

Example 17

Experimentals for Compound 31 of Scheme 22

Compound 30 (65 mg, 0.18 mmol) in dichloromethane (6 ml, anhydrous) whilst under $N_2$ was cooled to 0° C. in an ice bath and stirred for 10 minutes. Pyridine (0.07 mL) was added and the solution was stirred for 10 minutes. Methanesulphonyl chloride (1.17 eq, 25 mg, 0.21 mmol) was added dropwise and stirred for 1½ hours. A further 1 equivalence of methanesulphonyl chloride was added and the reaction was stirred for an hour and a half. The residue was allowed to warm to room temperature, a few drops of NaOH (3N) were added and then the compound was extracted with chloroform and dried over sodium sulfate. The organic layers were concentrated down and purified by column chromatography (3:1 dichloromethane/CMA) to yield the desired product 31 (22 mg, 28%): $^1$H NMR (300 MHz, MeOH) δ 8.31 (m, 1H), 8.29 (m, 1H), 7.35 (m, 1H), 7.28 (m, 1H), 7.15 (m, 1H), 4.43 (t, J=7.1 Hz, 2H), 4.20 (s, 2H), 2.98 (t, J=6.9 Hz, 2H), 2.92 (s, 3H), 2.73–2.56 (m, 4H), 1.02–0.97 (t, J=7.1 Hz, 6H) ppm.

Example 28

Experimentals for Compound 32 of Scheme 22

Compound 30 (57 mg, 0.16 mmol) in dichloromethane (5 mL) was cooled to 0° C. in an ice bath and stirred for 10 minutes, triethylamine (0.34 mmol, 0.047 mL) was added and the resulting solution was stirred for a further 15 minutes. Methyl chloroformate (23 mg, 0.24 mmol) was added dropwise and the mixture stirred for an hour. The ice bath was removed and stirred for a further half an hour. The ice bath was replaced and a further 0.5 equivalence of methyl chloroformate was then added. The ice bath was then removed and the mixture was stirred for 1½ hours. Water (5 mL) was added and the residue was basified to pH 9–10 with NaOH (6N). The resulting residue was then extracted with chloroform and dried over sodium sulfate. The organic layers were concentrated down and purified by column chromatography to give the pure desired product 32 (16 mg, 24%): $^1$H NMR (300 MHz, CDCl$_3$) δ 8.34 (m, 1H), 8.24 (m, 1H), 7.24 (m, 1H), 7.14 (m, 1H), 6.94 (d, J=8.6 Hz, 1H), 4.34 (m, 4H), 3.70 (s, 3H), 2.93 (t, J=7.1 Hz, 2H), 2.61–2.54 (m, 4H), 1.00 (t, J=7.1 Hz, 6H) ppm.

Example-29

Measuring the Inhibition of Cell Growth to Determine GI$_{50}$ Values

Growth inhibition (GI$_{50}$) values were measured with HeLa S-3 cells selected for growth on plastic. The procedure was based on the protocol of Skehan et al. (Skehan, P., et al., *J. Natl. Cancer Inst.*, 82:1107–1112 (1990), which is hereby incorporated by reference). HeLa cells were plated at 2×10$^4$ cells/well in 96 well plates. One day later, a control plate was fixed by addition of TCA to 5%. After five rinses with tap water, the plate was air dried and stored at 4° C. Test compounds were added to the remaining plates at 10-fold dilutions between 0.01 and 100 μM. Two days later, all plates were fixed as described above. Cells were then stained by the addition of 100 μl per well of 0.4% sulforhodamine B (SRB) in 1% acetic acid for 30 min at 4° C. Wells were then quickly rinsed 5× with acetic acid (1%) and allowed to air dry. The SRB was then solubilized by the addition of 100 μl per well of unbuffered 10 mM Tris base. Dye was quantified by measuring absorbance at 490 nm on a Molecular Devices kinetic microplate reader. Growth at each inhibitor concentration relative to the untreated control was calculated according to the following equation: percent growth=100×(T−T$_o$)/(C−T$_o$), where T was the average optical density (OD) of the test wells after 2 days of treatment, T$_o$ was the average OD of the wells in the control plate on day 0 and C was the average OD of untreated wells. Plots of percent growth versus inhibitor concentration were used to determine the GI$_{50}$.

The data below shown in Table 4 summarizes the in vitro cyclin/cdk inhibition constants (IC$_{50}$) of HeLa Cells for the compounds of the current invention. Replicate experimental results are summarized below.

TABLE 4

In Vitro Cyclin/cdk Inhibition (GI$_{50}$) of HeLa Cells For Compounds of the Present Invention.

| Compound | GI$_{50}$ Activity (μM) |
|---|---|
| (thioxanthone structure with HN-CH$_2$CH$_2$-N(Et)$_2$ substituent) | >10 |
| (thioxanthone structure with HN-CH$_2$CH$_2$-N(Et)$_2$ substituent and CHO group) | 2 |

TABLE 4-continued

In Vitro Cyclin/cdk Inhibition (GI$_{50}$) of HeLa Cells For Compounds of the Present Invention.

| Compound | GI$_{50}$ Activity ($\mu$M) |
|---|---|
| thioxanthone with 1-NH-CH$_2$CH$_2$-N(Et)$_2$ and 4-CH$_2$NHCHO | 3 |
| thioxanthone with 1-NH-CH$_2$CH$_2$-N(Et)$_2$ and 4-CH$_2$NH$_2$ | 0.6 |
| thioxanthone with 1-NH-CH$_2$CH$_2$-N(Et)$_2$ and 4-CH$_2$NHSO$_2$CH$_3$ | 3 |
| thioxanthone with 1-NH-CH$_2$CH$_2$-N(Et)$_2$ and 4-CH$_2$NHCO$_2$CH$_3$ | 3 |
| aza-thioxanthone with N(CH$_3$)-CH$_2$CH$_2$-N(Et)$_2$ substituent, x2HCl | >10 |

TABLE 4-continued

In Vitro Cyclin/cdk Inhibition ($GI_{50}$) of HeLa Cells For Compounds of the Present Invention.

| Compound | $GI_{50}$ Activity (μM) |
|---|---|
| (structure) x2HCl | 3 |
| (structure with CH₂NHCHO) | 1 |
| (structure with CH₂NH₂) | 0.7 |
| (structure with CH₂NHSO₂CH₃) x2HCl | 0.4 |
| (structure with CH₂NHCO₂CH₃) x2HCl | 0.3 |

TABLE 4-continued
In Vitro Cyclin/cdk Inhibition (GI$_{50}$) of HeLa Cells For Compounds of the Present Invention.
| Compound | GI$_{50}$ Activity ($\mu$M) |
|---|---|
| 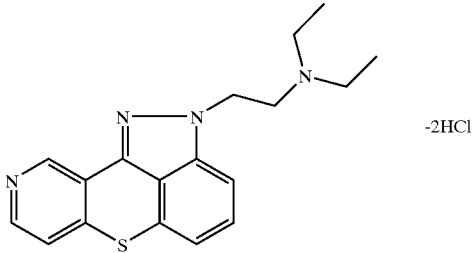 -2HCl | 1 |
| 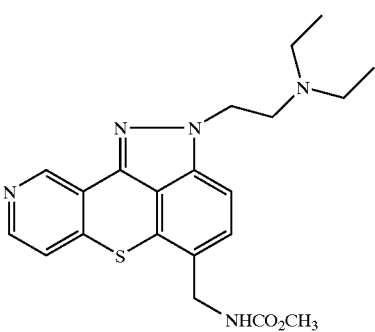 | 0.1 |
| 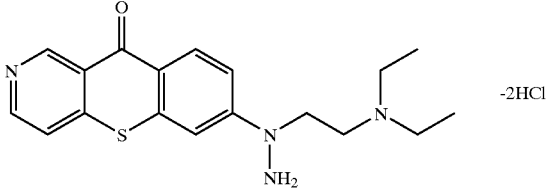 -2HCl | >10 |
| 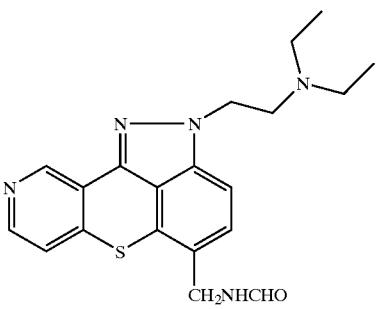 | 0.2 |
| 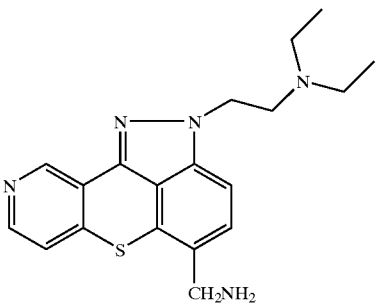 | 0.2 |

TABLE 4-continued
In Vitro Cyclin/cdk Inhibition ($GI_{50}$) of HeLa Cells For Compounds of the Present Invention.
| Compound | | $GI_{50}$ Activity ($\mu M$) |
|---|---|---|
| 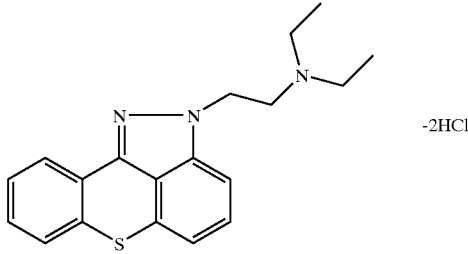 | -2HCl | 9 |
| 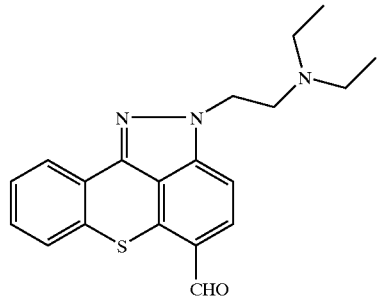 | | 2 |
| 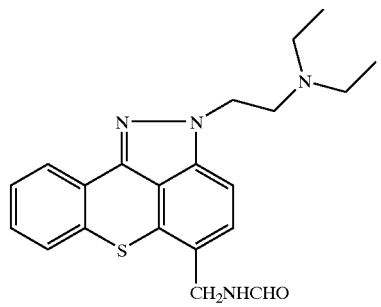 | | 1 |
| 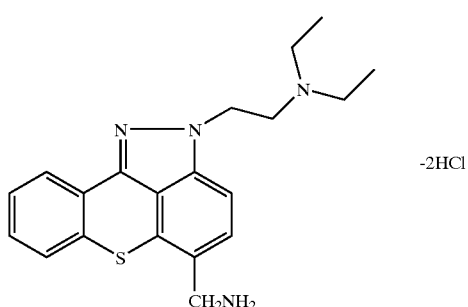 | -2HCl | 1 |
| 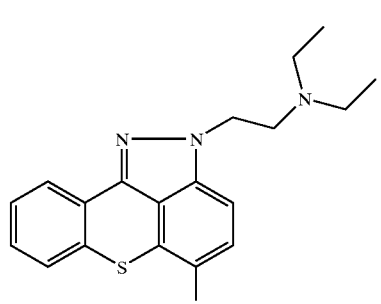 | | 0.9 |

TABLE 4-continued

In Vitro Cyclin/cdk Inhibition (GI$_{50}$) of HeLa Cells For Compounds of the Present Invention.

| Compound | GI$_{50}$ Activity ($\mu$M) |
| --- | --- |
| [structure: pyrazole-fused thiochromene with N-CH$_2$CH$_2$N(Et)$_2$ and CH$_2$NHCO$_2$CH$_3$ substituent] | 3 |
| | 20 |

Table 5 summarizes the data of tests performed to compare cyclin/cdk inhibition of HeLa cells resulting from the aza-analogs as compared to inhibition resulting from the carbocyclic congeners of the aza-analogs.

TABLE 5

Compares In Vitro Assay Results of Aza-Analogs and Their Carbocyclic Congeners, Measured According to Cyclin/cdk Inhibition(IC$_{50}$) of HeLa Cells

| Compound (carbocylic conogers) | IC$_{50}$ ($\mu$M) | Compound (aza-analogs) | IC$_{50}$ ($\mu$M) | Fold Improvement |
| --- | --- | --- | --- | --- |
| [thioxanthone with NH-CH$_2$CH$_2$N(Et)$_2$] | >10 | [aza-thioxanthone with NH-CH$_2$CH$_2$N(Et)$_2$] x2HCl | 3 | 3.5 |
| [thioxanthone with NH-CH$_2$CH$_2$N(Et)$_2$ and CH$_2$NHCHO] | 3 | [aza-thioxanthone with NH-CH$_2$CH$_2$N(Et)$_2$ and CH$_2$NHCHO] | 1 | 3 |
| [thioxanthone with NH-CH$_2$CH$_2$N(Et)$_2$ and CH$_2$NH$_2$] | 0.6 | [aza-thioxanthone with NH-CH$_2$CH$_2$N(Et)$_2$ and CH$_2$NH$_2$] | 0.7 | 1 |

TABLE 5-continued

Compares In Vitro Assay Results of Aza-Analogs and Their Carbocyclic Congeners, Measured According to Cyclin/cdk Inhibition($IC_{50}$) of HeLa Cells

| Compound (carbocylic conogers) | $IC_{50}$ ($\mu$M) | Compound (aza-analogs) | $IC_{50}$ ($\mu$M) | Fold Improvement |
|---|---|---|---|---|
| [structure with CH$_2$NHSO$_2$CH$_3$*] | 3 | [structure with CH$_2$NHSO$_2$CH$_3$] x2HCl | 0.4 | 7.5 |
| [structure with CH$_2$NHCO$_2$CH$_3$*] | 3 | [structure with CH$_2$NHCO$_2$CH$_3$] x2HCl | 0.3 | 10 |
| [pyrazole-fused structure] -2HCl | 9 | [aza-pyrazole-fused structure] -2HCl | 1 | 9 |
| [structure with CH$_2$NH$_2$] -2HCl | 1 | [structure with CH$_2$NH$_2$] | 0.2 | 5 |
| [structure with CH$_2$NHCHO] | 1 | [structure with CH$_2$NHCHO] | 0.2 | 5 |

TABLE 5-continued

Compares In Vitro Assay Results of Aza-Analogs and Their Carbocyclic Congeners, Measured According to Cyclin/cdk Inhibition($IC_{50}$) of HeLa Cells

| Compound (carbocylic conogers) | $IC_{50}$ ($\mu$M) | Compound (aza-analogs) | $IC_{50}$ ($\mu$M) | Fold Improvement |
|---|---|---|---|---|
| [structure, CH₂NHCO₂CH₃] | 3 | [structure, CH₂NHCO₂CH₃] | 0.1 | 30 |
| [structure, CH₂NHSO₂CH₃] | 0.9 | [structure, CH₂NHSO₂CH₃] | 0.3 | 3 |
| [structure, CH₂NHCO₂CH₃] | 3 | [structure, CH₂NHCO₂CH₃] | 0.5 | 6 |
| [structure, CH₂NHSO₂CH₃] | 0.9 | [structure, CH₂NHSO₂CH₃] | 0.3 | 3 |

TABLE 5-continued

Compares In Vitro Assay Results of Aza-Analogs and Their Carbocyclic Congeners, Measured According to Cyclin/cdk Inhibition($IC_{50}$) of HeLa Cells

| Compound (carbocylic conogers) | $IC_{50}$ ($\mu$M) | Compound (aza-analogs) | $IC_{50}$ ($\mu$M) | Fold Improvement |
|---|---|---|---|---|
| [structure with CH₂NH₂, ·2HCl] | 1 | [structure with CH₂NH₂, ·2HCl] | 0.2 | 5 |
| [structure with CH₂NHCHO] | 1 | [structure with CH₂NHCHO] | 0.5 | 2 |

Table 6 compares $GI_{50}$ results comparing aza-analogs having their nitrogen at different positions.

TABLE 6

Compares In Vitro Assay Results With Respect to the Nitrogen Position

| COMPOUND | $GI_{50}$ ($\mu$M) | COMPOUND | $GI_{50}$ ($\mu$M) | Folds |
|---|---|---|---|---|
| [structure with CH₂NH₂] | 0.2 | [structure with CH₂NH₂, ·2HCl] | 0.2 | 1 |

TABLE 6-continued

Compares In Vitro Assay Results With Respect to the Nitrogen Position

| COMPOUND | GI$_{50}$ (μM) | COMPOUND | GI$_{50}$ (μM) | Folds |
|---|---|---|---|---|
| (structure with CH$_2$NHCHO) | 0.05 | (structure with CH$_2$NHCHO) | 0.5 | 10 |
| (structure with CH$_2$NHCO$_2$CH$_3$) | 0.1 | (structure with CH$_2$NHCO$_2$CH$_3$) | 0.5 | 5 |
| (structure with CH$_2$NHSO$_2$CH$_3$) | 0.2 | (structure with CH$_2$NHSO$_2$CH$_3$) | 0.3 | 1.5 |
| (structure with CH$_3$) •2HCl | 0.1 | (structure with CH$_3$) •2HCl | 0.6 | 6 |

TABLE 6-continued

Compares In Vitro Assay Results With Respect to the Nitrogen Position

| COMPOUND | GI$_{50}$ (μM) | COMPOUND | GI$_{50}$ (μM) | Folds |
|---|---|---|---|---|
| 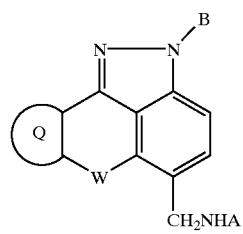 | 0.4 | 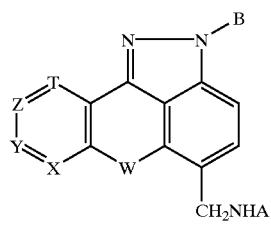 | 3.0 | 7.5 |

GI$_{50}$ is the concentration of the compound that causes 50 percent inhibition of tumor cell growth.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound having the formula:

where:
- W is selected from the group consisting of S, SO, and SO$_2$;
- Q is a 5- or 6-membered aromatic ring having at least one atom selected from the group consisting of N and S;
- A is selected from the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; C(O)H; C(O)OR$_1$; SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;
- B is selected in the group consisting of: hydrogen; C$_1$–C$_4$ linear, branched, or cyclic alkyl which is substituted or unsubstituted; C$_1$–C$_4$ linear or branched alkoxy which is substituted or unsubstituted; hydroxy; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;
- R$_1$ is selected from a group consisting of C$_1$–C$_{10}$ alkyl, phenyl, and phenyl alkyl, as free bases;
- n is 2–3;
- m is 0–3;
- p is 0–3; and
- D is selected from the group consisting of: hydroxy; C$_1$–C$_4$ linear or branched alkoxy which is substituted or unsubstituted; and a 5- or 6-member aromatic or non-aromatic heterocyclic ring containing a sulfur, oxygen, or nitrogen heteroatom or pharmaceutically acceptable salts.

2. A compound according to claim 1, where the compound has the following formula:

(II)

where:

one or more of X, Y, Z, or T=N; or a pharmaceutically acceptable salt thereof.

3. A compound according to claim 2, where the compound has the following formula:

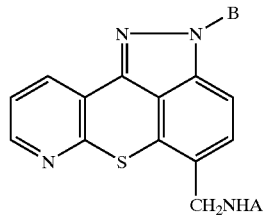

or a pharmaceutically acceptable salt thereof.

4. A compound according to claim 2, where the compound has the following formula:

or a pharmaceutically acceptable salt thereof.

5. A compound according to claim 2, where the compound has the following formula:

[structure with CH₂NHA]

or a pharmaceutically acceptable salt thereof.

6. A compound according to claim 2, where the compound has the following formula:

[structure with W and CH₂NHA]

or a pharmaceutically acceptable salt thereof.

7. A compound according to claim 1, where the compound has the following formula:

[structure with NHB and CH₂NHA]

a pharmaceutically acceptable salt thereof.

8. A compound according to claim 1, where the compound has the following formula:

[structure with X, Y, Z and CH₂NHA]

where:
X, Y, or Z=S; or
a pharmaceutically acceptable salt thereof.

9. A compound according to claim 8, where the compound has the following formula:

[structure with CH₂NHA]

or a pharmaceutically acceptable salt thereof.

10. A compound according to claim 8, where the compound has the following formula:

[structure with CH₂NHA]

or a pharmaceutically acceptable salt thereof.

11. A compound according to claim 8, where the compound has the following formula:

[structure with CH₂NHA]

or a pharmaceutically acceptable salt thereof.

12. A process for preparation of a product compound of the formula:

(II)

[structure with Z, T, Y, X, W, B and CH₂NHA]

where:
one or more of X, Y, Z, or T=N;
W is selected from the group consisting of S, SO, and SO₂;
A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H, C(O)OR₁, SO₂R₁; $(CH_2)_n NH(CH_2)_m CH_3$; $(CH_2)_n N((CH_2)_m CH_3)(CH_2)_p CH_3$; and $(CH_2)_n D$;
B is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy;

$(CH_2)_nNH(CH_2)_mCH_3$; $(CH_2)_nN((CH_2)_mCH_3)(CH_2)_pCH_3$; and $(CH_2)_nD$;

$R_1$ is selected from a group consisting of $C_1-C_{10}$ alkyl, phenyl, and phenyl alkyl, as free bases;

n is 2–3;

m is 0–3;

p is 0–3; and

D is selected from the group consisting of: hydroxy; $C_1-C_4$ linear or branched alkoxy which is substituted or unsubstituted; and a 5- or 6-member aromatic or non-aromatic heterocyclic ring containing a sulfur, oxygen, or nitrogen heteroatom; or pharmaceutically acceptable salts thereof, said process comprising:

transforming a first intermediate compound of the formula:

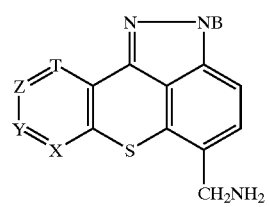

7 under conditions effective to form the product compound.

13. The process according to claim 12 further comprising:
reacting a second intermediate compound of the formula:

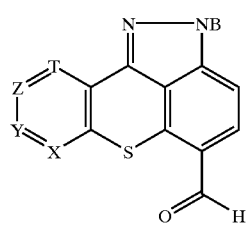

6 with formamide/formic acid under conditions effective to form the first intermediate compound.

14. The process according to claim 13 further comprising:
reacting a third intermediate compound of the formula:

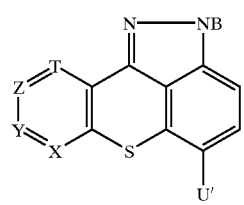

5a under conditions effective to form the second intermediate compound, wherein U' is I, F, Cl, Br, or H.

15. The process according to claim 14 further comprising:
reacting a fourth intermediate compound of the formula:

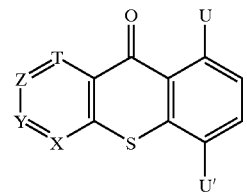

4a where U is I, Br, F or Cl,
in the presence of $NH_2NHB$, under conditions effective to form a mixture comprising the third intermediate compound.

16. The process according to claim 15 further comprising:
reacting a fifth intermediate compound of the formula:

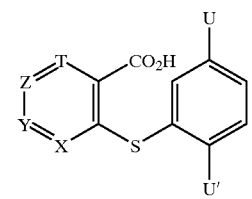

3 under conditions effective to form a mixture comprising the fourth intermediate compound.

17. The process according to claim 16, further comprising:
reacting a sixth intermediate compound of the formula:

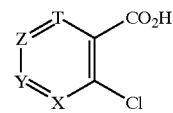

with a seventh intermediate compound of the formula:

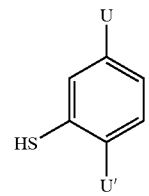

under conditions effective to form the fifth intermediate compound.

18. The process according to claim 16 further comprising:
reacting an eighth intermediate compound of the formula:

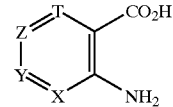

with $NaNO_2$ and HU under conditions effective to form the sixth intermediate compound.

19. The process according to claim 18 further comprising:

reacting a ninth intermediate compound of the formula:

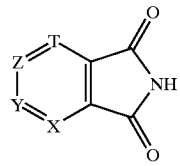

under conditions effective to form the eighth intermediate compound.

20. The process according to claim 19 further comprising:

reacting a tenth intermediate compound of the formula:

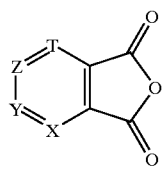

under conditions effective to form the ninth intermediate compound.

21. The process according to claim 20 further comprising:

reacting an eleventh intermediate compound of the formula:

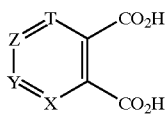

under conditions effective to form the tenth intermediate compound.

22. The process according to claim 21, where Y=N.
23. The process according to claim 21, where T=N.
24. The process according to claim 21 further comprising:

reacting the product compound under conditions effective to form a second product compound having the formula:

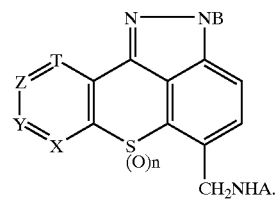

25. A process according to claim 15, where Z=Y=N, and where said fourth intermediate compound is prepared by the process comprising:

reacting a fifteenth intermediate compound of the formula:

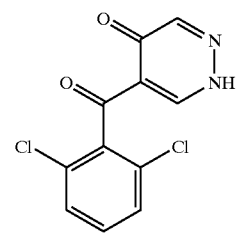

with $P_2S_5$-pyridine under conditions effective to form the fourth intermediate compound.

26. The process according to claim 25 further comprising:

reacting a sixteenth intermediate compound of the formula:

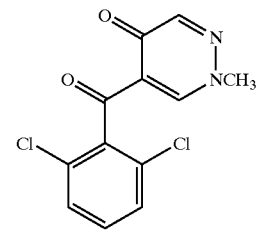

with $AlCl_3$-toulene under conditions effective to form the fifteenth intermediate compound.

27. The process according to claim 26 further comprising:

reacting a seventeenth intermediate compound of the formula:

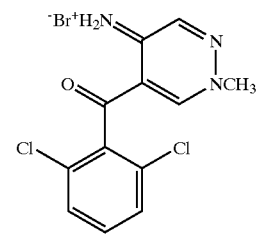

under conditions effective to form the fifteenth intermediate compound.

28. The process according to claim 27 further comprising:

reacting a eighteenth intermediate compound of the formula:

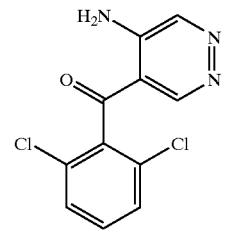

under conditions effective to form the seventeenth intermediate compound.

29. The process according to claim 28 further comprising:

reacting an nineteenth intermediate compound of the formula:

under conditions effective to form the eighteenth intermediate compound.

30. The process according to claim 29 further comprising:

reacting a twentieth intermediate compound of the formula:

under conditions effective to form the nineteenth intermediate compound.

31. The process according to claim 30 further comprising:

reacting a twenty-first intermediate compound of the formula:

under conditions effective to form the twentieth intermediate compound.

32. The process according to claim 31 further comprising:

reacting a twenty-second intermediate compound of the formula:

with a twenty-third intermediate compound of the formula:

under conditions effective to form the twenty-first intermediate compound.

33. A process for preparation of a product compound of the formula:

where:

A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H; C(O)OR$_1$; SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;

B is selected in the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; (CH$_2$)$_n$NH (CH$_2$)$_m$CH$_3$; (CH$_2$)$_n$N((CH$_2$)$_m$CH$_3$)(CH$_2$)$_p$CH$_3$; and (CH$_2$)$_n$D;

R$_1$ is selected from a group consisting of $C_1$–$C_{10}$ alkyl, phenyl, and phenyl alkyl, as free bases;

n is 2–3;

m is 0–3;

p is 0–3; and

D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom; or a pharmaceutically acceptable salt thereof, said process comprising:

transforming a first intermediate compound of the formula:

under conditions effective to form the product compound.

34. The process according to claim 33 further comprising:
reacting a second intermediate compound of the formula:

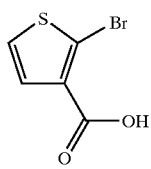

under conditions effective to form the first intermediate compound.

35. The process according to claim 34 further comprising:
reacting a third intermediate compound of the formula:

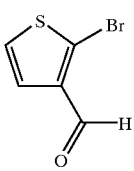

under conditions effective to form the second intermediate compound.

36. The process according to claim 35 further comprising:
reacting a fourth intermediate compound of the formula:

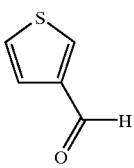

under conditions effective to form the third intermediate compound.

37. A process for preparation of a product compound of the formula:

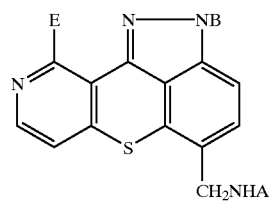

where:
A is selected from the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; C(O)H; C(O)OR$_1$; SO$_2$R$_1$; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;
B is selected in the group consisting of: hydrogen; $C_1$–$C_4$ linear, branched, or cyclic alkyl which is substituted or unsubstituted; $C_1$–$C_4$ linear or branched alkoxy which is substituted or unsubstituted; hydroxy; (CH$_2$)$_n$NH(CH$_2$)$_m$CH$_3$; (CH$_2$)$_n$N((CH$_2$)$_m$CH$_3$)(CH$_2$)$_p$CH$_3$; and (CH$_2$)$_n$D;
$R_1$ is selected from a group consisting of $C_1$–$C_{10}$ alkyl, phenyl, and phenyl alkyl, as free bases;
n is 2–3;
m is 0–3;
p is 0–3;
E is OCH$_3$ or Cl; and
D is selected from the group consisting of: hydroxy; $C_1$–$C_4$ linear or branched alkoxy which is substituted or unsubstituted; and a 5- or 6-member aromatic or non-aromatic heterocyclic ring containing a sulfur, oxygen, or nitrogen heteroatom; or
a pharmaceutically acceptable salt thereof, said process comprising:
transforming a first intermediate compound of the formula:

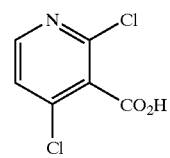

under conditions effective to form the product compound wherein E is Cl.

38. The process according to claim 37 further comprising:
reacting a second intermediate compound of the formula:

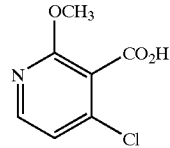

under conditions effective to form the first intermediate compound.

39. The process according to claim 38 further comprising:
reacting a second intermediate compound of the formula:

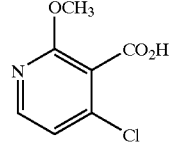

under conditions effective to form the product compound, where E is OCH$_3$.

40. The process according to claim 38 further comprising:
reacting a third intermediate compound of the formula:

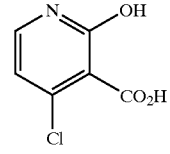

under conditions effective to form the second intermediate compound.

41. The process according to claim 40 further comprising:
reacting a fourth intermediate compound of the formula:

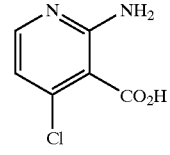

under conditions effective to form the third intermediate compound.

42. The process according to claim 41 further comprising: reacting a fifth intermediate compound of the formula:

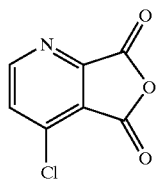

under conditions effective to form the fourth intermediate compound.

43. The process according to claim 42 further comprising: reacting a sixth intermediate compound of the formula:

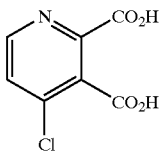

under conditions effective to form the fifth intermediate compound.

44. The process according to claim 43 further comprising: reacting a seventh intermediate compound of the formula:

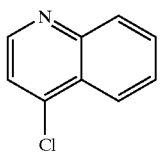

under conditions effective to form the sixth intermediate compound.

45. The process according to claim 44 further comprising: reacting a eighth intermediate compound of the formula:

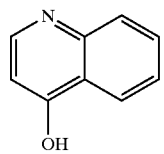

under conditions effective to form the seventh intermediate compound.

46. A method for inhibiting cell proliferation in mammals comprising:

administering a therapeutically effective amount of the compound of claim 1 to the mammal.

47. The method of claim 46, where the compound is administered to a mammal suffering from a cell proliferation disorder selected from the group consisting of rheumatoid arthritis, lupus, type 1 diabetes, multiple sclerosis, cancer, restenosis, gout, and other proliferative diseases involving abnormal cellular proliferation.

48. The method of claim 47, where the cellular proliferation disorder is cancer.

49. The method of claim 47, where the cellular proliferation disorder is restenosis.

50. The method of claim 47, where the cellular proliferation disorder is type 1 diabetes.

51. The method of claim 47, where the mammal is human.

52. A pharmaceutical composition of matter comprising the compound of claim 1 and one or more pharmaceutical excipients.

* * * * *